(12) United States Patent
Ronan et al.

(10) Patent No.: US 7,560,571 B2
(45) Date of Patent: Jul. 14, 2009

(54) SUBSTITUTED PYRROLES AND IMIDAZOLES, COMPOSITIONS CONTAINING SAME, MANUFACTURING PROCESS THEREFOR AND USE THEREOF

(75) Inventors: Baptiste Ronan, Clamart (FR); Frank Halley, Chaville (FR); Catherine Souaille, Choisy le Roi (FR); Fabrice Viviani, Louvres (FR); Youssef El-Ahmad, Creteil (FR); Eric Bacque, Gif sur Yvette (FR); Michel Tabart, La Norville (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 11/832,206

(22) Filed: Aug. 1, 2007

(65) Prior Publication Data

US 2008/0045542 A1 Feb. 21, 2008

Related U.S. Application Data

(63) Continuation of application No. PCT/FR2006/000220, filed on Feb. 1, 2006.

(30) Foreign Application Priority Data

Feb. 3, 2005 (FR) .................................. 05 01092

(51) Int. Cl.
*C07D 233/64* (2006.01)
*C07D 207/30* (2006.01)
*C07D 207/46* (2006.01)

(52) U.S. Cl. .................................... 548/335.5; 548/537
(58) Field of Classification Search ............. 548/335.5, 548/537

See application file for complete search history.

(56) References Cited

U.S. PATENT DOCUMENTS

| 2004/0138269 A1 | 7/2004 | Sun et al. |
| 2004/0220229 A1 * | 11/2004 | Bussolotti et al. ........... 514/339 |
| 2005/0261354 A1 | 11/2005 | Griffin et al. |

FOREIGN PATENT DOCUMENTS

| CA | 2 546 334 | 6/2005 |
| WO | WO 02/079193 A1 | 10/2002 |
| WO | WO 03/072541 A2 | 9/2003 |
| WO | WO 2005/049603 A1 | 6/2005 |
| WO | WO 2006/084996 A1 | 8/2006 |

OTHER PUBLICATIONS

U.S. Appl. No. 11/832,208, filed Aug. 1, 2007, Ronan et al.

* cited by examiner

*Primary Examiner*—Rebecca L Anderson
*Assistant Examiner*—Shawquia Young
(74) *Attorney, Agent, or Firm*—Kelly L. Bender

(57) ABSTRACT

The disclosure concerns substituted imidazoles and pyrroles, compositions containing the same, the preparation thereof, and the use thereof as medicaments, particularly as anti-cancer agents.

19 Claims, No Drawings

SUBSTITUTED PYRROLES AND IMIDAZOLES, COMPOSITIONS CONTAINING SAME, MANUFACTURING PROCESS THEREFOR AND USE THEREOF

The present invention relates especially to novel chemical compounds, particularly novel substituted pyrroles and imidazoles, to compositions containing them and to their use as medicaments.

More particularly, the invention relates to novel specific pyrroles and imidazoles with anticancer activity, via modulation of the activity of proteins, in particular kinases.

At the present time, most of the commercial compounds used in chemotherapy present considerable problems of side effects and of patient tolerance. These effects might be limited if the medicaments used act selectively on cancer cells, without touching healthy cells. One of the solutions for limiting the adverse effects of a chemotherapy may thus consist in using medicaments that act on metabolic pathways or on constituent elements of these pathways, expressed predominantly in cancer cells, and which are expressed little or not at all in healthy cells.

Protein kinases are a family of enzymes that catalyse the phosphorylation of hydroxyl groups of specific residues of proteins, such as tyrosine, serine or threonine residues. Such phosphorylations may greatly modify the function of the proteins; thus, protein kinases play an important role in regulating a wide variety of cell processes including, especially, metabolism, cell proliferation, cell differentiation, cell migration and cell survival. Among the various cellular functions in which the activity of a protein kinase is involved, certain processes represent attractive targets for treating cancer cells and also other diseases.

Thus, one of the objects of the present invention is to propose compositions with anticancer activity, by acting in particular with respect to kinases. Among the kinases for which modulation of the activity is desired, FAK, KDR and Tie2 are preferred.

These products correspond to formula (I) below:

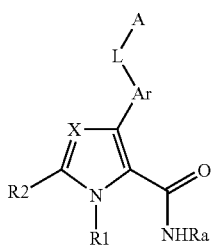

Formula (I)

in which:
1) A and Ar are independently selected from the group consisting of: aryl, heteroaryl, heterocyclyl, substituted aryl, substituted heteroaryl, substituted heterocyclyl, cycloalkyl, substituted cycloalkyl
2) L is selected from the group consisting of: NH, CO—NH, NH—CO, NH—SO$_2$, SO$_2$NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, NH—CO—O, O—CO—NH, CH$_2$—NH—CO—NH, NH—CO—NH—CH$_2$, NH—CO—CH$_2$—CO—NH;
3) Ra is selected from the group consisting of H, alkyl and cycloalkyl.
4) R1 is selected from the group consisting of: H, R, COR, SO$_2$R, in which R is chosen from H, OR"$_4$, NR"$_5$R"$_6$, (C1-C6)alkyl, cycloalkyl, heterocyclyl, substituted heterocyclyl, aryl, substituted aryl, heteroaryl and substituted heteroaryl, in which R"4 is chosen from H, phenyl and alkyl, and in which R"5 and R"6 are independently selected from the group consisting of H, R OR"$_4$, (C1-C6)alkyl, cycloalkyl, heterocyclyl, substituted heterocyclyl, aryl, substituted aryl, heteroaryl and substituted heteroaryl, or alternatively R"5 and R"6 are linked together to form a saturated 5- to 8-membered ring containing from 0 to 3 hetero atoms chosen from O, S and N;
5) X is chosen from CR3 and N;
6) R2 and R3 are independently selected from the group consisting of: H, halogen, R'2, CN, O(R'2), OC(O)(R'2), OC(O)N(R'2)(R'3), OS(O$_2$)(R'2), N(R'2)(R'3), N=C(R'2)(R'3), N(R'2)C(O)(R'3), N(R'2)C(O)O(R'3), N(R'4)C(O)N(R'2)(R'3), N(R'4)C(S)N(R'2)(R'3), N(R'2)S(O$_2$)(R'3), C(O)(R'2), C(O)O(R'2), C(O)N(R'2)(R'3), C(=N(R'3))(R'2), C(=N(OR'3))(R'2), S(R'2), S(O)(R'2), S(O$_2$)(R'2), S(O$_2$)O(R'2), S(O$_2$)N(R'2)(R'3); in which each R'2, R'3, R'4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl and substituted heterocyclyl; in which, when R'2 and R'3 are each other than H and simultaneously present on R2 or on R3, they may be linked together to form a ring containing from 0 to 3 hetero atoms chosen from O, S and N.

In the products of formula (I), Ar—L-A is advantageously:

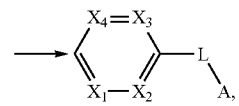

in which each X1, X2, X3 and X4 is independently chosen from N and C—R'5, in which R'5 has the same definition as R2.

Substituents R'5 selected from the group consisting of H, F, Cl, methyl, NH$_2$, OMe, OCF$_3$ and CONH$_2$ are preferred.

R2 is preferentially H.

Preferred products according to the invention are those for which X is CR3. At least one from among R2 and R3 is preferentially a halogen.

R3 is also preferably selected from the group consisting of H, halogen, NH$_2$, N(R'2)C(O)(R'3), N(R'2)C(O)O(R'3), N(R'4)C(O)N(R'2)(R'3), C(O)O(R'2) and C(O)N(R'2)(R'3); in which each R'2, R'3 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl and substituted heterocyclyl; in which, when R'2 and R'3 are each other than H and simultaneously present on R2 or on R3, they may be linked together to form a ring containing from 0 to 3 hetero atoms chosen from O, S and N.

R3 is more preferentially selected from the group consisting of H, halogen, NH$_2$, NH—COO-alkyl and —NH—CO—NH-aryl in which the aryl is unsubstituted or substituted with one or more halogen or haloalkyl, —NH—CO-alkyl, —NH—CO-alkyl-N(alkyl)(alkyl'), —COOH, —COO-alkyl, —COO-alkyl-N(alkyl)(alkyl') or —CO—NH-alkyl-aryl in which the aryl is unsubstituted or substituted with one or more alkoxy, —CONH₂ or —CO-heterocyclyl in which the heterocyclyl is unsubstituted or substituted with one or more alkyls.

R1 is preferentially H. Ra is preferentially H.

Preferred substituents L-A are advantageously chosen from NH—CO—NH-A and NH—SO₂-A.

A combination L-A that is particularly effective is obtained when L-A is NHCONH-A.

Products in accordance with the invention preferably have a substituent A that is selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl and benzothiazolyl; optionally substituted.

More preferably, A is chosen from phenyl, pyrazolyl and isoxazolyl; optionally substituted.

The substituent A is very advantageously substituted with a first substituent chosen from the group consisting of alkyl, substituted alkyl, alkylene, alkynyl, aryl, heteroaryl, O-alkyl, substituted O-alkyl, O-Aryl, O-heteroaryl, S-alkyl, substituted S-alkyl, S-Aryl and S-heteroaryl, each being optionally substituted with a substituent chosen from (C1-C3)alkyl, halogen and O—(C1-C3)alkyl.

The substituent A is preferentially substituted with a second substituent chosen from the group consisting of F, Cl, Br, I, OH, SH, SO₃M, COOM, CN, NO₂, CON(R8)(R9), N(R8)CO(R9), (C1-C3)alkyl-OH, (C1-C3)alkyl-N(R8)(R9), (C1-C3)alkyl-(R10), (C1-C3)alkyl-COOH and N(R8)(R9); in which R8 and R9 are independently chosen from H, (C1-C3)alkyl, (C1-C3)haloalkyl, (C1-C3)alkylOH, (C1-C3)alkylNH₂, (C1-C3)alkylCOOM and (C1-C3)alkylSO₃M; in which, when R8 and R9 are simultaneously other than H, they may be linked together to form a 5- to 7-membered ring optionally containing from 1 to 3 hetero atoms; in which M is H or a cation of an alkali metal chosen from Li, Na and K; and in which R10 is H or an optionally substituted non-aromatic heterocycle, containing 2 to 7 carbon atoms and 1 to 3 hetero atoms chosen from N, O and S.

Particularly preferred substituents A are chosen from phenyl, pyrazolyl and isoxazolyl; the said substituents A possibly being substituted with halogen, (C1-C4)alkyl, (C1-C3)haloalkyl, O—(C1-C4)alkyl, S—(C1-C4)alkyl, O—(C1-C4)haloalkyl and S—(C1-C4)haloalkyl. When A is disubstituted, the two substituents of A may form a 5- to 7-membered ring optionally containing from 1 to 3 hetero atoms.

Other preferred substituents A are substituted with one or more substituents, which may be identical or different, independently selected from the group consisting of F, Cl, Br, I, OH, SH, SO₃M, COOM, CN, NO₂, CON(R8)(R9), N(R8)CO(R9), (C1-C3)alkyl-OH, (C1-C3)alkyl-N(R8)(R9), (C1-C3)alkyl-(R10), (C1-C3)alkyl-COOH, N(R8)(R9), (C1-C6)alkyl, (C2-C6)alkylene, (C2-C6)alkynyl, aryl, heteroaryl, O—(C1-C6)alkyl, O-Aryl, O-heteroaryl, S—(C1-C6)alkyl, S-Aryl and S-heteroaryl, each being optionally substituted with one or more substituents chosen from (C1-C3)alkyl, halogen and O—(C1-C3)alkyl; in which R8 and R9 are independently chosen from H, (C1-C3)alkyl, (C1-C3)alkylOH, (C1-C3)alkylNH₂, (C1-C3)alkylCOOM and (C1-C3)alkylSO₃M; in which, when R8 and R9 are simultaneously other than H, they may be linked together to form a 5- to 7-membered ring containing from 0 to 3 hetero atoms chosen from O, N and S; in which M is H or a cation of an alkali metal chosen from Li, Na and K; and in which R10 is H or an optionally substituted non-aromatic heterocycle, containing 2 to 7 carbon atoms and 1 to 3 hetero atoms chosen from N, O and S.

Preferred products according to the present invention are chosen from:

3-{4-[3-(2-Fluoro-5-trifluoromethylphenyl)ureido]phenyl}-1H-pyrrole-2-carboxamide, 4-tert-Butyloxycarbonylamino-3-{4-[3-(2-fluoro-5-trifluoromethylphenyl)-ureido]phenyl}-1H-pyrrole-2-carboxamide, 4-Amino-3-{4-[3-(2-fluoro-5-trifluoromethylphenyl)ureido]phenyl}-1H-pyrrole-2-carboxamide hydrochloride, 4-[3-(2-Fluoro-5-trifluoromethylphenyl)ureido]-3-{4-[3-(2-fluoro-5-trifluoro-methylphenyl)ureido]phenyl}-1H-pyrrole-2-carboxamide, 4-Acetylamino-3-{4-[3-(2-fluoro-5-trifluoromethylphenyl)ureido]phenyl}-1H-pyrrole-2-carboxamide, 4-(2-Dimethylaminoacetylamino)-3-{4-[3-(2-fluoro-5-trifluoromethylphenyl)-ureido]phenyl}-1H-pyrrole-2-carboxamide, 4-Benzoylamino-3-{4-[3-(2-fluoro-5-trifluoromethylphenyl)ureido]phenyl}-1H-pyrrole-2-carboxamide, 4-Nicotinoylamino-3-{4-[3-(2-fluoro-5-trifluoromethylphenyl)ureido]phenyl}-1H-pyrrole-2-carboxamide, Ethyl 5-carbamoyl-4-{4-[3-(2-fluoro-5-trifluoromethylphenyl)ureido]phenyl}-1H-pyrrole-3-carboxylate, Ethyl 5-carbamoyl-4-{4-[3-(2-fluorophenyl)ureido]phenyl}-1H-pyrrole-3-carboxylate, Ethyl 5-carbamoyl-4-{4-[3-(2-methoxyphenyl)ureido]phenyl}-1H-pyrrole-3-carboxylate, Ethyl 5-carbamoyl-4-{4-[3-(2-trifluoromethylphenyl)ureido]phenyl}-1H-pyrrole-3-carboxylate, Ethyl 5-carbamoyl-4-[4-(3-o-tolylureido)phenyl]-1H-pyrrole-3-carboxylate, Ethyl 5-carbamoyl-4-{4-[3-(3-fluorophenyl)ureido]phenyl}-1H-pyrrole-3-carboxylate, Ethyl 5-carbamoyl-4-{4-[3-(3-methoxyphenyl)ureido]phenyl}-1H-pyrrole-3-carboxylate, Ethyl 5-carbamoyl-4-{4-[3-(3-trifluoromethylphenyl)ureido]phenyl}-1H-pyrrole-3-carboxylate, Ethyl 5-carbamoyl-4-[4-(3-m-tolylureido)phenyl]-1H-pyrrole-3-carboxylate, Ethyl 5-carbamoyl-4-{4-[3-(4-fluorophenyl)ureido]phenyl}-1H-pyrrole-3-carboxylate, Ethyl 5-carbamoyl-4-{4-[3-(4-methoxyphenyl)ureido]phenyl}-1H-pyrrole-3-carboxylate, Ethyl 5-carbamoyl-4-{4-[3-(4-trifluoromethylphenyl)ureido]phenyl}-1H-pyrrole-3-carboxylate, Ethyl 5-carbamoyl-4-[4-(3-p-tolylureido)phenyl]-1H-pyrrole-3-carboxylate, Ethyl 5-carbamoyl-4-{4-[3-(4-chloro-3-trifluoromethylphenyl)ureido]phenyl}-1H-pyrrole-3-carboxylate, Ethyl 5-carbamoyl-4-{4-[3-(2-chloro-5-trifluoromethylphenyl)ureido]phenyl}-1H-pyrrole-3-carboxylate, Ethyl 5-carbamoyl-4-{4-[3-(2-fluoro-3-trifluoromethylphenyl)ureido]phenyl}-1H-pyrrole-3-carboxylate, Ethyl 5-carbamoyl-4-{4-[3-(4-fluoro-3-trifluoromethylphenyl)ureido]phenyl}-1H-pyrrole-3-carboxylate, Ethyl 5-carbamoyl-4-{4-[3-(3-fluoro-5-trifluoromethylphenyl)ureido]phenyl}-1H-pyrrole-3-carboxylate, Ethyl 5-carbamoyl-4-{4-[3-(4-methyl-3-trifluoromethylphenyl)ureido]phenyl}-1H-pyrrole-3-carboxylate, Ethyl 5-carbamoyl-4-{4-[3-(4-trifluoromethoxyphenyl)ureido]phenyl}-1H-pyrrole-3-carboxylate, Ethyl 5-carbamoyl-4-{4-[3-(4-difluoromethoxyphenyl)ureido]phenyl}-1H-pyrrole-3-carboxylate, Ethyl 5-carbamoyl-4-{4-[3-(3,4-dimethylphenyl)ureido]phenyl}-1H-pyrrole-3-carboxylate, Ethyl 5-carbamoyl-4-{4-[3-(3,4-dimethoxyphenyl)ureido]phenyl}-1H-pyrrole-3-carboxylate, Ethyl 5-carbamoyl-4-{4-[3-(3,5-dimethoxyphenyl)ureido]phenyl}-1H-pyrrole-3-carboxylate,
Ethyl 5-carbamoyl-4-{4-[3-(2,5-dimethylphenyl)ureido]phenyl}-1H-pyrrole-3-carboxylate,
Ethyl 5-carbamoyl-4-{4-[3-(2-methoxy-5-methylphenyl)ureido]phenyl}-1H-pyrrole-3-carboxylate,
Ethyl 5-carbamoyl-4-{4-[3-(2,5-dimethoxyphenyl)ureido]phenyl}-1H-pyrrole-3-carboxylate,
Ethyl 5-carbamoyl-4-{4-[3-(3-chloro-4-difluoromethoxyphenyl)ureido]phenyl}-1H-pyrrole-3-carboxylate,
Ethyl 5-carbamoyl-4-{4-[3-(3,5-dimethylphenyl)ureido]phenyl}-1H-pyrrole-3-carboxylate,
5-Carbamoyl-4-{4-[3-(2-fluoro-5-trifluoromethylphenyl)ureido]phenyl}-1H-pyrrole-3-carboxylic acid,
4-(2,4-Dimethoxybenzylamino)carbonyl-3-{4-[3-(2-fluoro-5-trifluoromethyl-phenyl)ureido]phenyl}-1H-pyrrole-2-carboxamide,
3-{4-[3-(2-Fluoro-5-trifluoromethylphenyl)ureido]phenyl}-1H-pyrrole-2,4-dicarboxamide,
3-{4-[3-(2-Fluoro-5-trifluoromethylphenyl)ureido]phenyl}-4-(4-methylpiperazine-1-carbonyl)-1H-pyrrole-2-carboxamide,
3-{4-[3-(2-Fluoro-5-trifluoromethylphenyl)ureido]phenyl}-4-(pyrrolidine-1-carbonyl)-1H-pyrrole-2-carboxamide,
2-Dimethylaminoethyl 5-carbamoyl-4-{4-[3-(2-fluoro-5-trifluoromethylphenyl)-ureido]phenyl}-1H-pyrrole-3-carboxylate,
4-Chloro-3-{4-[3-(2-fluoro-5-trifluoromethylphenyl)ureido]phenyl}-1H-pyrrole-2-carboxamide,
5-Chloro-3-{4-[3-(2-fluoro-5-trifluoromethylphenyl)ureido]phenyl}-1H-pyrrole-2-carboxamide,
5-{4-[3-(2-Fluoro-5-trifluoromethylphenyl)ureido]phenyl}-3H-imidazole-4-carboxamide.

A product in accordance with the invention may be:
1) in achiral form, or
2) in racemic form, or
3) enriched in one stereoisomer, or
4) enriched in one enantiomer;

and may be optionally salified.

A product in accordance with the invention may be used for the manufacture of a medicament that is useful for treating a pathological condition, in particular a cancer.

The present invention also relates to therapeutic compositions comprising a product according to the invention, in combination with a pharmaceutically acceptable excipient according to the chosen mode of administration. The pharmaceutical composition may be in solid or liquid form or in the form of liposomes.

Among the solid compositions that may be mentioned are powders, gel capsules and tablets. Among the oral forms that may also be included are solid forms protected with respect to the acidic medium of the stomach. The supports used for the solid forms consist especially of mineral supports, for instance phosphates or carbonates, or organic supports, for instance lactose, celluloses, starch or polymers. The liquid forms consist of solutions, suspensions or dispersions. They contain as dispersive support either water or an organic solvent (ethanol, NMP or the like) or mixtures of surfactants and of solvents, or of complexing agents and of solvents.

The liquid forms will preferably be injectable and, as a result, will have a formulation that is acceptable for such a use.

Routes of administration that are acceptable by injection include intravenous, intraperitoneal, intramuscular and subcutaneous routes, the intravenous route usually being preferred.

The administered dose of the compounds of the invention will be adapted by the practitioner as a function of the route of administration to the patient and of the patient's condition.

The compounds of the present invention may be administered alone or as a mixture with other anticancer agents. Among the possible combinations that may be mentioned are:

alkylating agents and especially cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine platinum derivatives such as, especially, cisplatin, carboplatin or oxaliplatin antibiotics such as, especially, bleomycin, mitomycin or dactinomycin antimicrotubule agents such as, especially, vinblastine, vincristine, vindesine, vinorelbine and taxoids (paclitaxel and docetaxel)

anthracyclines such as, especially, doxorubicin, daunorubicin, idarubicin, epirubicin, mitoxantrone and losoxantrone group I and II topoisomerase inhibitors such as etoposide, teniposide, amsacrine, irinotecan, topotecan and tomudex fluoropyrimidines such as 5-fluorouracil, UFT and floxuridine cytidine analogues such as 5-azacytidine, cytarabine, gemcitabine, 6-mercaptomurine and 6-thioguanine adenosine analogues such as pentostatin, cytarabine or fludarabine phosphate methotrexate and folinic acid various enzymes and compounds such as L-asparaginase, hydroxyurea, trans-retinoic acid, suramine, dexrazoxane, amifostine and herceptin, and also oestrogen-based and androgenic hormones antivascular agents such as combretastatin derivatives, for example CAP4P, chalcones or colchicine derivatives, for example ZD6126, and prodrugs thereof.

It is also possible to combine the compounds of the present invention with a radiation treatment. These treatments may be administered simultaneously, separately or sequentially. The treatment will be adapted by the practitioner as a function of the patient to be treated.

The products of the invention are useful as inhibitors of a reaction catalysed by a kinase. FAK, KDR and Tie2 are kinases for which the products of the invention will be particularly useful as inhibitors.

The reasons for which these kinases are chosen are given below:

FAK

FAK is a cytoplasmic tyrosine kinase that plays an important role in transducing the signal transmitted by the integrins, a family of heterodimeric cellular adhesion receptors. FAK and the integrins are colocated in perimembrane structures known as adhesion plaques. It has been shown in many cell types that the activation of FAK and its phosphorylation on tyrosine residues and in particular its autophosphorylation on tyrosine 397 were dependent on the binding of integrins to their extracellular ligands and thus induced during cellular adhesion [Kornberg L, et al. J. Biol. Chem. 267(33): 23439-442 (1992)]. Autophosphorylation on tyrosine 397 of FAK represents a binding site for another tyrosine kinase, Src, via its SH2 domain [Schaller et al. Mol. Cell. Biol. 14: 1680-1688 1994; Xing et al. Mol. Cell. Biol. 5: 413-421 1994]. Src may then phosphorylate FAK on tyrosine 925, thus recruiting the adapter protein Grb2 and inducing in certain cells activation of the ras and MAP kinase pathway involved in controlling cell proliferation [Schlaepfer et al. Nature; 372: 786-791. 1994; Schlaepfer et al. Prog. Biophy. Mol. Biol. 71: 435-478. 1999; Schlaepfer and Hunter, J. Biol. Chem. 272: 13189-13195 1997]. The activation of FAK may also induce the jun NH2-terminal kinase (JNK) signalling pathway and result in the progression of cells towards the G1 phase of the cell cycle [Oktay et al., J. Cell. Biol. 145: 1461-1469 1999]. Phosphatidylinositol-3-OH kinase (PI3-kinase) also binds to FAK on tyrosine 397 and this interaction might be necessary for activating PI3-kinase [Chen and Guan, Proc. Nat. Acad. Sci. USA. 91: 10148-10152. 1994; Ling et al. J. Cell. Biochem. 73: 533-544. 1999]. The FAK/Src complex phosphorylates various substrates, for instance paxillin and p130CAS in fibroblasts [Vuori et al. Mol. Cell. Biol. 16: 2606-2613. 1996].

The results of numerous studies support the hypothesis that FAK inhibitors might be useful in treating cancer. Studies have suggested that FAK might play an important role in cell proliferation and/or survival in vitro. For example, in CHO cells, some authors have demonstrated that the overexpression of p125FAK leads to an acceleration of the transition G1 to S, suggesting that p125FAK promotes cell proliferation [Zhao J.-H et al. J. Cell Biol. 143: 1997-2008. 1998]. Other authors have shown that tumour cells treated with FAK antisense oligonucleotides lose their adhesion and enter into apoptosis (Xu et al., Cell Growth Differ. 4: 413-418. 1996). It has also been demonstrated that FAK promotes the migration of cells in vitro. Thus, fibroblasts that are deficient for FAK expression (FAK "knockout" mice) show a rounded morphology and deficiencies in cellular migration in response to chemotactic signals, and these defects are eliminated by re-expression of FAK [D J. Sieg et al., J. Cell Science. 112: 2677-91. 1999]. Overexpression of the C-terminal domain of FAK (FRNK) blocks the stretching of adherent cells and reduces cell migration in vitro [Richardson A. and Parsons J. T. Nature. 380: 538-540. 1996]. Overexpression of FAK in CHO or COS cells or in human astrocytoma cells promotes migration of the cells. The involvement of FAK in promotion of the proliferation and migration of cells in many cell types in vitro suggests the potential role of FAK in neoplastic processes. A recent study has effectively demonstrated the increase in the proliferation of tumour cells in vivo after inducing the expression of FAK in human astrocytoma cells [Cary L. A. et al. J. Cell Sci. 109: 1787-94 1996; Wang D et al. J. Cell Sci. 113: 4221-4230. 2000]. Furthermore, immunohistochemical studies of human biopsies have demonstrated that FAK was overexpressed in prostate cancer, breast cancer, thyroid cancer, colon cancer, melanoma, brain cancer and lung cancer, the level of expression of FAK being directly correlated to the tumours showing the most aggressive phenotype [Weiner T M, et al. Lancet. 342 (8878): 1024-1025. 1993; Owens et al. Cancer Research. 55: 2752-2755. 1995; Maung K. et al. Oncogene. 18: 6824-6828. 1999; Wang D et al. J. Cell Sci. 113: 4221-4230. 2000].

KDR

KDR (Kinase insert Domain Receptor), also known as VEGF-R2 (Vascular Endothelial Growth Factor Receptor 2), is expressed solely in endothelial cells. This receptor binds to the angiogenic growth factor VEGF, and thus serves as a transduction signal mediator via the activation of its intracellular kinase domain. The direct inhibition of the kinase activity of VEGF-R2 makes it possible to reduce the phenomenon of angiogenesis in the presence of exogenous VEGF (Vascular Endothelial Growth Factor) (Strawn et al., *Cancer Research*, 1996, vol. 56, p. 3540-3545). This process has especially been demonstrated using VEGF-R2 mutants (Millauer et al., *Cancer Research*, 1996, vol. 56, p. 1615-1620). The VEGF-R2 receptor appears to have no other function in adults than that associated with the angiogenic activity of VEGF. Thus, a selective inhibitor of the kinase activity of VEGF-R2 should show only little toxicity.

In addition to this central role in the dynamic angiogenic process, recent results suggest that the expression of VEGF contributes towards the survival of tumoral cells after chemotherapy and radiotherapy, underlining the potential synergy of KDR inhibitors with other agents (Lee et al. *Cancer Research*, 2000, vol. 60, p. 5565-5570).

Tie2

Tie-2 (TEK) is a member of a family of tyrosine kinase receptors, which is specific to endothelial cells. Tie2 is the first receptor with tyrosine kinase activity for which both the agonist (angiopoietin 1 or Ang1), which stimulates the autophosphorylation of the receptor and cell signalling [S. Davis et al. (1996) Cell 87, 1161-1169], and the antagonist (angiopoietin 2 or Ang2) [P. C. Maisonpierre. (1997) Science 277, 55-60] are known. Angiopoietin 1 can synergize with VEGF in the final stages of neoangiogenesis [Asahara T. Circ. Res. (1998) 233-240]. Knock-out experiments and transgenic manipulations of the expression of Tie2 or of Ang1 lead to animals that present vascularization defects [D. J. Dumont et al. (1994) Genes Dev. 8, 1897-1909 and C. Suri (1996) Cell 87, 1171-1180]. The binding of Ang1 to its receptor leads to autophosphorylation of the kinase domain of Tie2, which is essential for neovascularization and also for the recruitment and interaction of blood vessels with the pericytes and smooth muscle cells; these phenomena contribute towards the maturation and stability of the newly formed blood vessels [P. C. Maisonpierre et al. (1997) Science 277, 55-60]. Lin et al. (1997) J. Clin. Invest. 100, 8: 2072-2078 and Lin P. (1998) PNAS 95, 8829-8834 have shown an inhibition of tumour growth and vascularization, and also a reduction in lung metastases, during adenoviral infections or injections of the extracellular domain of Tie-2 (Tek) into models of melanoma and breast tumour xenografts.

Tie2 inhibitors may be used in situations in which neovascularization takes place inappropriately (i.e. in diabetic retinopathy, chronic inflammation, psoriasis, Kaposi's sarcoma, chronic neovascularization due to macular degeneration, rheumatoid arthritis, infantile haemoangioma and cancers).

Definitions

The term "halogen" refers to an element chosen from F, Cl, Br and I.

The term "alkyl" refers to a linear or branched saturated hydrocarbon-based substituent containing from 1 to 12 carbon atoms. The substituents methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl are examples of alkyl substituents.

The term "alkylene" refers to a linear or branched hydrocarbon-based substituent containing one or more unsaturations, and containing from 2 to 12 carbon atoms. The substituents ethylenyl, 1-methylethylenyl, prop-1-enyl, prop-2-enyl, Z-1-methylprop-1-enyl, E-1-methylprop-1-enyl, Z-1,2-dimethyl-prop-1-enyl, E-1,2-dimethylprop-1-enyl, but-1,3-dienyl, 1-methylidenylprop-2-enyl, Z-2-methylbut-1,3-dienyl, E-2-methylbut-1,3-dienyl, 2-methyl-1-methylidenylprop-2-enyl, undec-1-enyl and undec-10-enyl are examples of alkylene substituents.

The term "alkynyl" refers to a linear or branched hydrocarbon-based substituent containing at least two unsaturations borne by a pair of vicinal carbon atoms, and containing from 2 to 12 carbon atoms. The substituents ethynyl; prop-1-ynyl; prop-2-ynyl; and but-1-ynyl are examples of alkynyl substituents.

The term "aryl" refers to a monocyclic or polycyclic aromatic substituent containing from 6 to 14 carbon atoms. The substituents phenyl, naphth-1-yl; naphth-2-yl; anthracen-9-yl; 1,2,3,4-tetrahydronaphth-5-yl; and 1,2,3,4-tetrahydronaphth-6-yl are examples of aryl substituents.

The term "heteroaryl" refers to a monocyclic or polycyclic heteroaromatic substituent containing from 1 to 13 carbon atoms and from 1 to 4 hetero atoms. The substituents pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinolyl; isoquinolyl; carbazolyl; and acridyl are examples of heteroaryl substituents.

The term "hetero atom" refers herein to an at least divalent atom other than carbon. N; O; S; and Se are examples of hetero atoms.

The term "cycloalkyl" refers to a saturated or partially unsaturated cyclic hydrocarbon-based substituent containing from 3 to 12 carbon atoms. The substituents cyclopropyl; cyclobutyl; cyclopentyl; cyclopentenyl; cyclopentadienyl; cyclohexyl; cyclohexenyl; cycloheptyl; bicyclo[2.2.1]heptyl; cyclooctyl; bicyclo[2.2.2]octyl; adamantyl; and perhydronapthyl are examples of cycloalkyl substituents.

The term "heterocyclyl" refers to a saturated or partially unsaturated cyclic hydrocarbon-based substituent containing from 1 to 13 carbon atoms and from 1 to 4 hetero atoms. Preferably, the saturated or partially unsaturated cyclic hydrocarbon-based substituent will be monocyclic and will contain 4 or 5 carbon atoms and 1 to 3 hetero atoms.

The term "substituted" refers to one or more substituents other than H, for example halogen; alkyl; haloalkyl; aryl; aryl substituted with one or more alkoxy groups; heteroaryl, cycloalkyl; heterocyclyl; alkylene; alkynyl; OH; O-alkyl; O-alkylene; O-aryl; O-heteroaryl; $NH_2$; NH-alkyl; NH-aryl; NH-heteroaryl; N-alkyl-alkyl'; SH; S-alkyl; S-aryl; $S(O_2)H$; $S(O_2)$-alkyl; $S(O_2)$-aryl; $SO_3H$; $SO_3$-alkyl; $SO_3$-aryl; CHO; C(O)-alkyl; C(O)-aryl; C(O)OH; C(O)O-alkyl; C(O)O-aryl; OC(O)-alkyl; OC(O)-aryl; $C(O)NH_2$; C(O)NH-alkyl; C(O)NH-aryl; NHCHO; NHC(O)-alkyl; NHC(O)-aryl; NH-cycloalkyl; NH-heterocyclyl.

A subject of the present invention is also the process for preparing the products of formula (I).

The products according to the invention may be prepared using conventional methods of organic chemistry. Scheme 1 below illustrates the method used for the preparation of Example 1 concerning the substituted pyrroles. In this respect, it cannot constitute a limitation of the scope of the invention, as regards the methods for preparing the claimed compounds.

Scheme 1

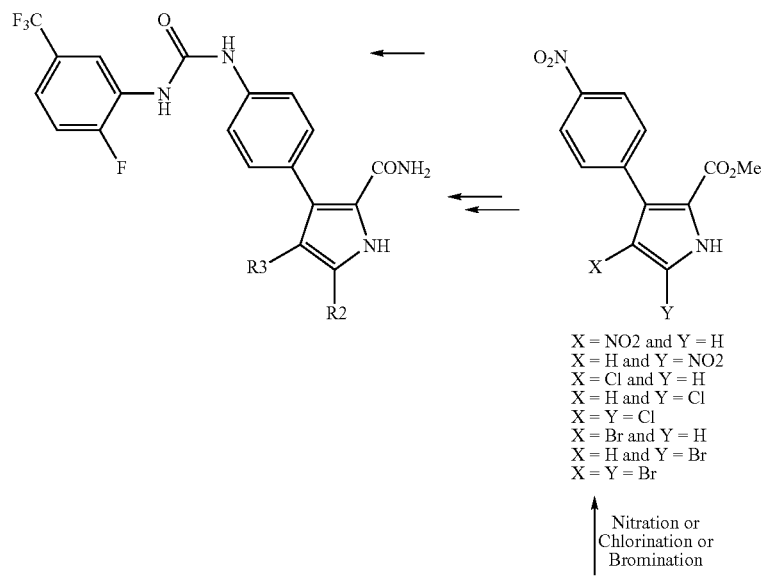

X = NO2 and Y = H
X = H and Y = NO2
X = Cl and Y = H
X = H and Y = Cl
X = Y = Cl
X = Br and Y = H
X = H and Y = Br
X = Y = Br Nitration or
Chlorination or
Bromination

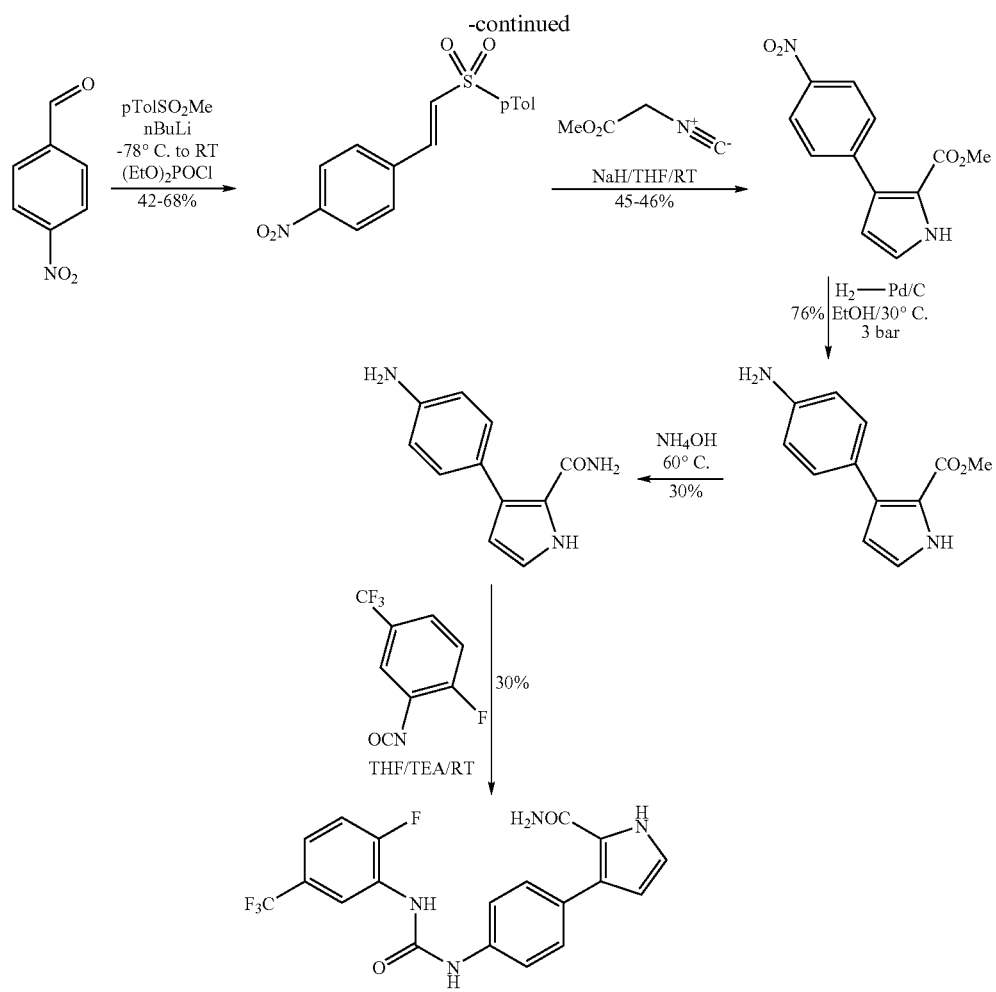
The schemes below illustrate the methods used for the preparation of the examples concerning the substituted imidazoles. In this respect, they cannot constitute a limitation of the scope of the invention, as regards the methods for preparing the claimed compounds.
Scheme 2
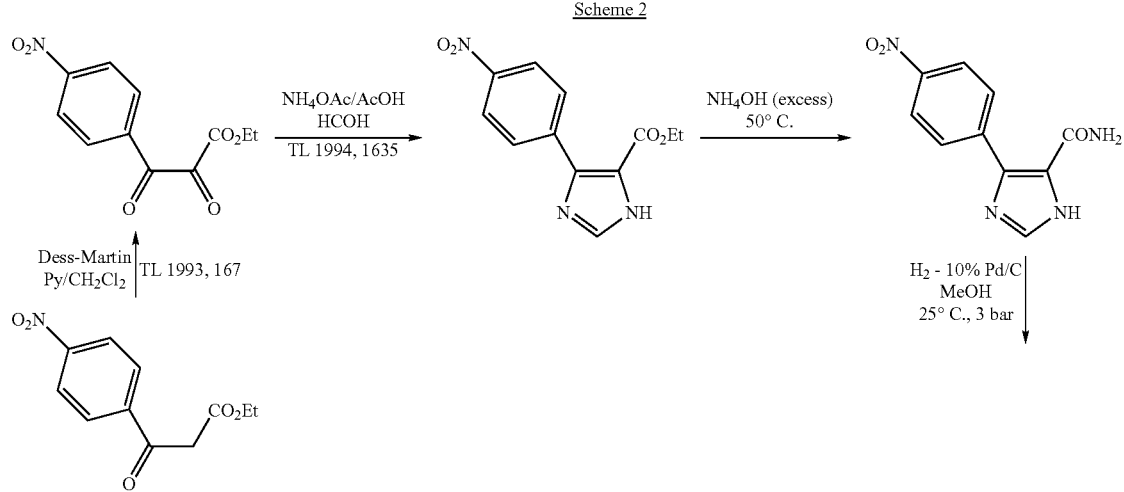

-continued
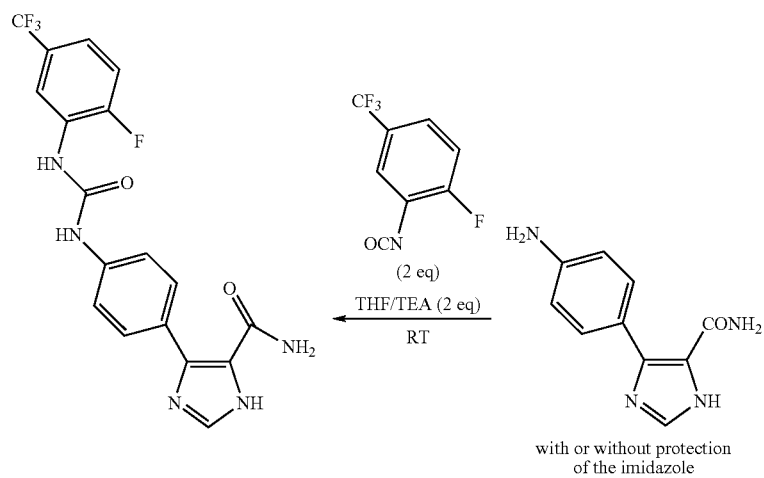
Scheme 3
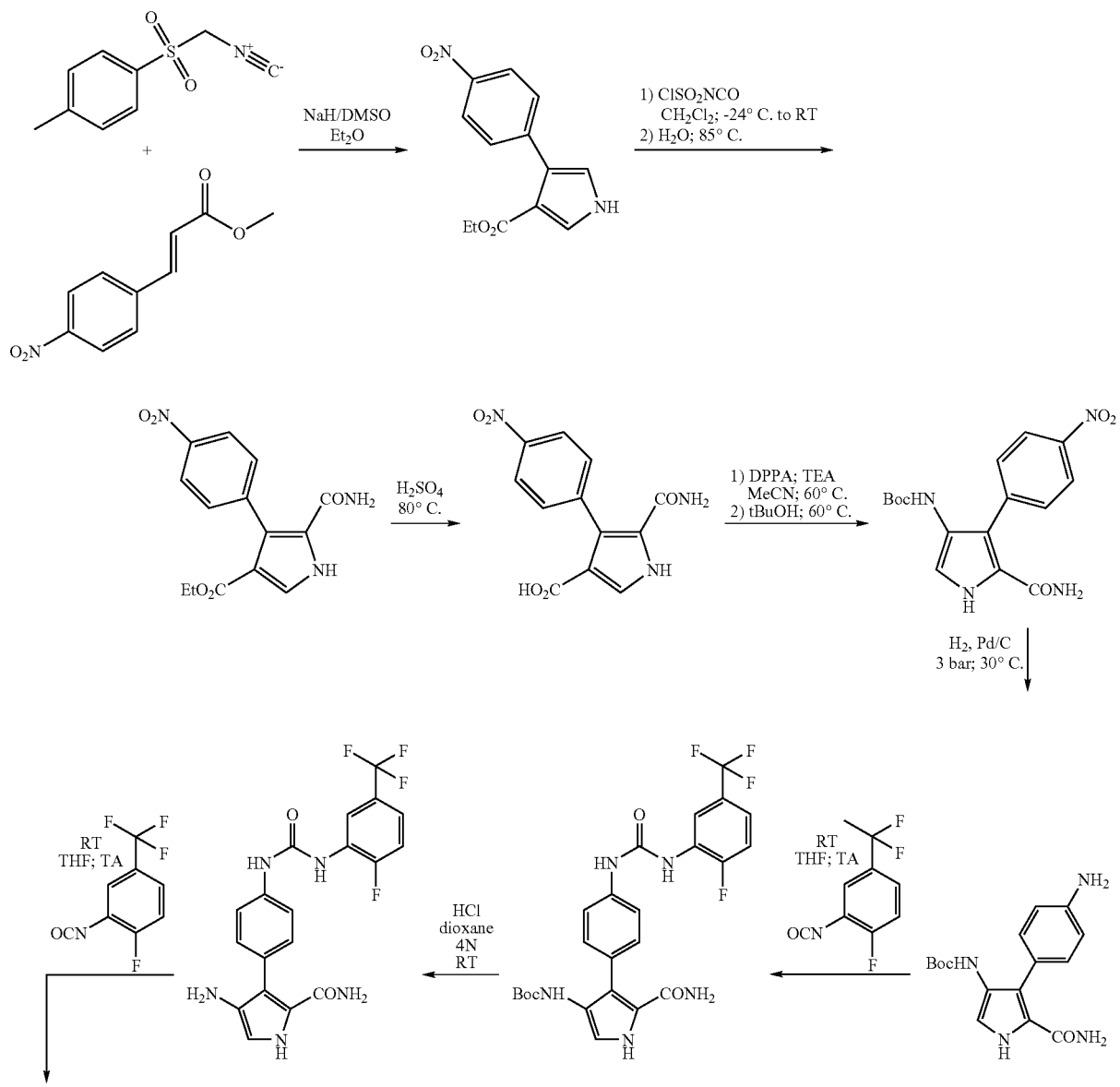

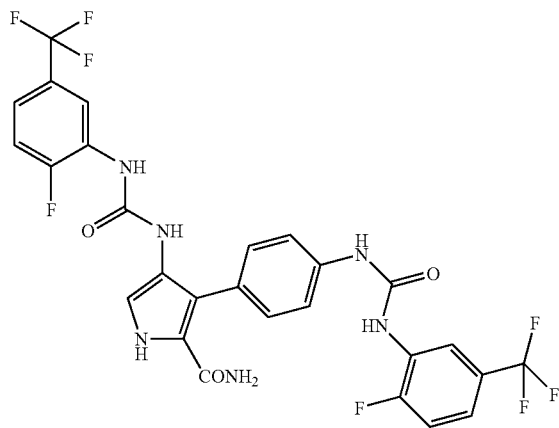
Scheme 4
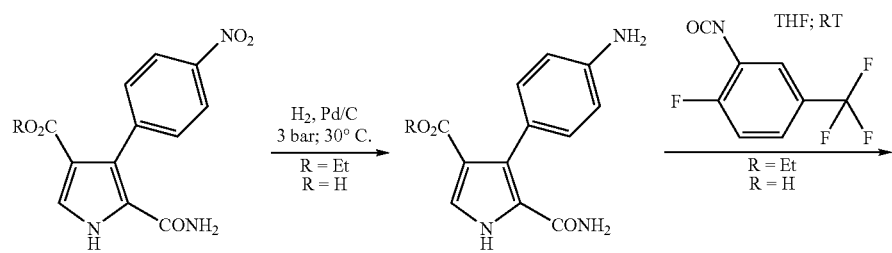
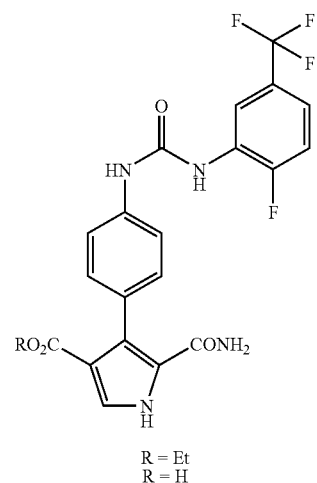
R = Et
R = H
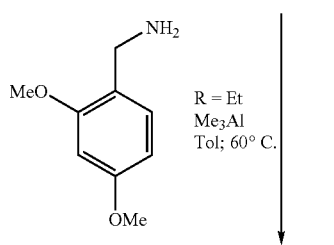
R = Et
Me₃Al
Tol; 60° C.

-continued

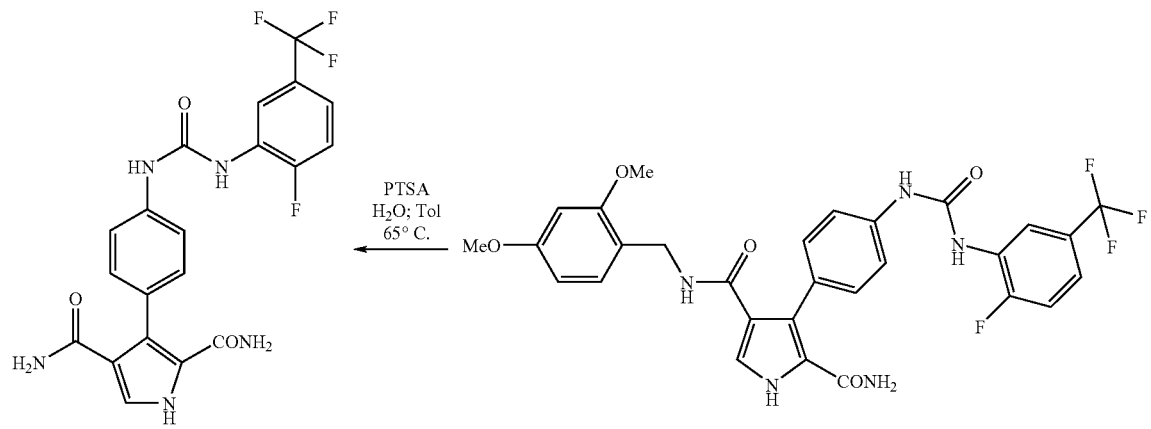

Scheme 5

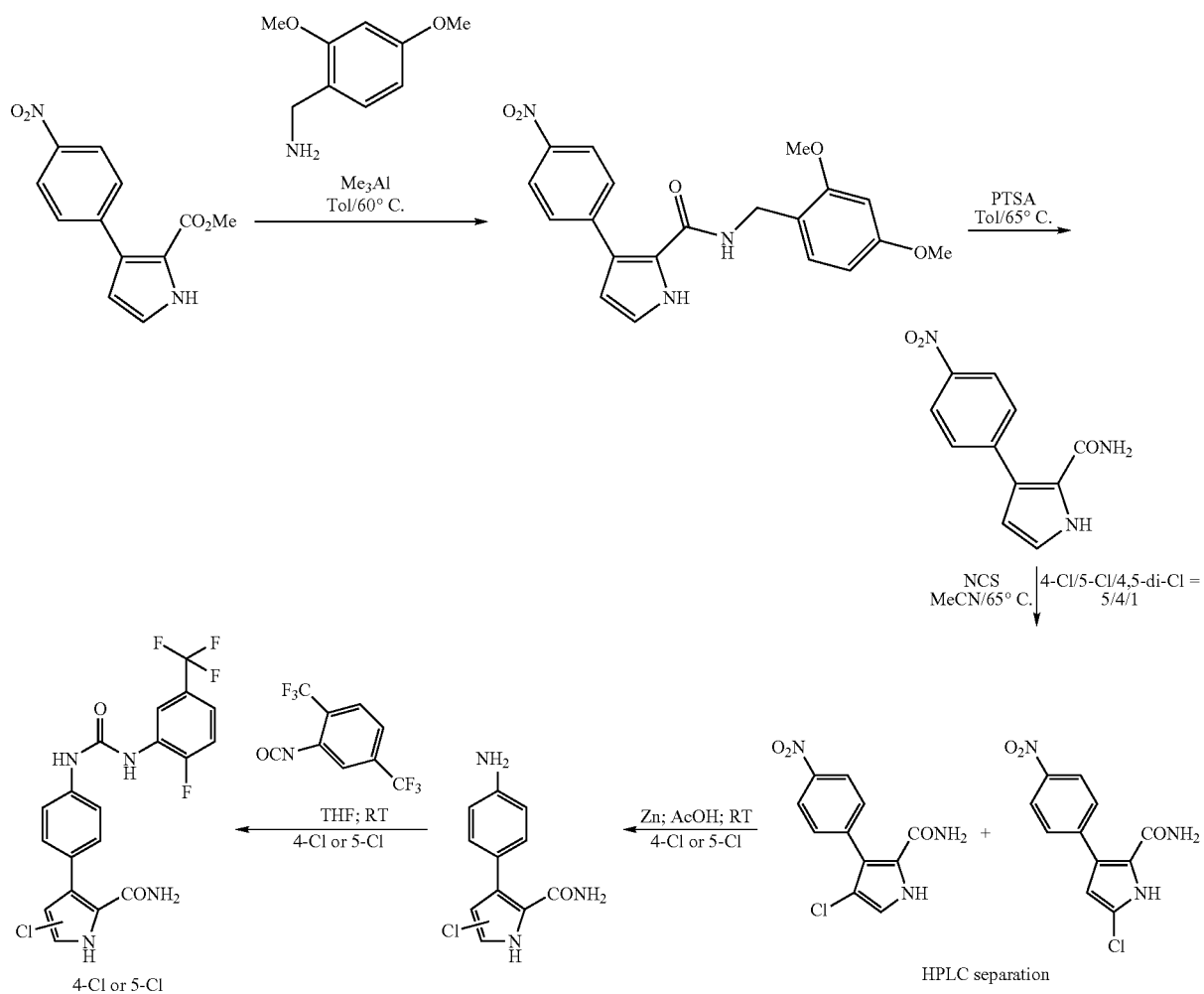

It is understood by a person skilled in the art that, for the implementation of the processes according to the invention described above, it may be necessary to introduce protecting groups for the amino, carboxyl and alcohol functions in order to avoid side reactions. These groups are those that can be removed without affecting the rest of the molecule. As examples of protecting groups for the amino function, mention may be made of tert-butyl carbamate, which may be regenerated using trifluoroacetic acid or iodotrimethylsilane, and acetyl, which may be regenerated in acidic medium (for example hydrochloric acid). As protecting groups for the carboxyl function, mention may be made of esters (for example methoxymethyl ester or benzyl ester). As protecting groups for the alcohol function, mention may be made of esters (for example benzoyl ester), which may be regenerated in acidic medium or by catalytic hydrogenation. Other protecting groups that may be used are described by T. W. Greene et al. in Protective Groups in Organic Synthesis, third edition, 1999, Wiley-Interscience.

The compounds of formula (I) are isolated and may be purified by means of the usual known methods, for example by crystallization, chromatography or extraction.

The enantiomers and diastereoisomers of the compounds of formula (I) also form part of the invention.

The compounds of formula (I) comprising a basic residue may be optionally converted into addition salts with a mineral or organic acid, via the action of such an acid in a solvent, for example an organic solvent such as an alcohol, a ketone, an ether or a chlorinated solvent.

The compounds of formula (I) comprising an acid residue may be optionally converted into metal salts or into addition salts with nitrogen bases according to methods that are known per se. These salts may be obtained via the action of a metallic base (for example an alkali metal or alkaline-earth metal base), ammonia, an amine or an amine salt on a compound of formula (I), in a solvent. The salt formed is separated out via the usual methods.

These salts also form part of the invention.

When a product according to the invention contains at least one free basic function, pharmaceutically acceptable salts may be prepared by reaction between the said product and a mineral or organic acid. Pharmaceutically acceptable salts include chlorides, nitrates, sulfates, hydrogen sulfates, pyrosulfates, bisulfates, sulfites, bisulfites, phosphates, monohydrogen phosphates, dihydrogen phosphates, metaphosphates, pyrophosphates, acetates, propionates, acrylates, 4-hydroxybutyrates, caprylates, caproates, decanoates, oxalates, malonates, succinates, glutarates, adipates, pimelates, maleates, fumarates, citrates, tartrates, lactates, phenylacetates, mandelates, sebacates, suberates, benzoates, phthalates, methanesulfonates, p-toluenesulfonate, propanesulfonates, xylenesulfonates, salicylates, cinnamates, glutamates, aspartates, glucuronates and galacturonates.

When a product according to the invention contains at least one free acid function, pharmaceutically acceptable salts may be prepared by reaction between the said product and a mineral or organic base. Pharmaceutically acceptable bases include hydroxides of cations of alkali metals or alkaline-earth metals such as Li, Na, K, Mg or Ca, and basic amino compounds such as ammonia, arginine, histidine, piperidine, morpholine, piperazine or triethylamine.

The invention is also described by the examples that follow, which are given as illustrations of the invention.

The LC/MS analyses were performed on an LCT Micromass machine connected to an HP 1100 machine. The abundance of the products was measured using an HP G1315A diode array detector over a wavelength range of 200-600 nm and a Sedex 65 light scattering detector. The mass spectra were acquired over a range from 180 to 800. The data were analysed using the Micromass MassLynx software. The separation was performed on a Hypersil BDS C18 3 µm (50×4.6 mm) column, eluting with a linear gradient of 5% to 90% acetonitrile containing 0.05% (v/v) of trifluoroacetic acid (TFA) in water containing 0.05% (v/v) of TFA, over 3.5 minutes at a flow rate of 1 ml/minute. The total analysis time, including the column reequilibration period, is 7 minutes.

The mass spectra were acquired in electrospray ($ES^+$) mode on a Plafform II (Micromass) machine. The main ions observed are described.

The melting points were measured by capillary, on a Mettler FP62 machine, over the range 30° C. to 300° C., with a temperature rise of 2° C. per minute.

Purification by LC/MS:

The products may be purified by LC/MS using a Waters FractionsLynx system composed of a Waters 600 gradient pump, a Waters 515 regeneration pump, a Waters Reagent Manager dilution pump, a Waters 2700 auto-injector, two Rheodyne LabPro valves, a Waters 996 diode array detector, a Waters ZMD mass spectrometer and a Gilson 204 fraction collector. The system was controlled by the Waters FractionLynx software. The separation was performed alternately on two Waters Symmetry ($C_{18}$, 5 µM, 19×50 mm, catalogue reference 186000210) columns, one column undergoing regeneration with a 95/5 (v/v) water/acetonitrile mixture containing 0.07% (v/v) of trifluoroacetic acid, while the other column was being used for separation. The columns were eluted using a linear gradient of 5% to 95% acetonitrile containing 0.07% (v/v) of trifluoroacetic acid in water containing 0.07% (v/v) of trifluoroacetic acid, at a flow rate of 10 ml/minute. On leaving the separation column, one thousandth of the effluent is separated out using an LC Packing Accurate machine, diluted with methanol at a flow rate of 0.5 ml/minute and conveyed to the detectors, in a proportion of 75% to the diode array detector and the remaining 25% to the mass spectrometer. The rest of the effluent (999/1000) is conveyed to the fraction collector, where the flow is discarded if the mass of the expected product is not detected by the FractionLynx software. The molecular formulae of the expected products are supplied to the FractionLynx software, which triggers the collection of the product when the mass signal detected corresponds to the $[M+H]^+$ ion and/or to the $[M+Na]^+$ ion. In certain cases, depending on the analytical LC/MS results, when an intense ion corresponding to $[M+2H]^{++}$ was detected, the value corresponding to half the calculated molecular mass (MW/2) is also supplied to the FractionLynx software. Under these conditions, collection is also triggered when the mass signal of the $[M+2H]^{++}$ and/or $[M+Na+H]^{++}$ ion is detected. The products were collected in tared glass tubes. After collection, the solvents were evaporated off, in a Savant AES 2000 or Genevac HT8 centrifugal evaporator and the masses of the products were determined by weighing the tubes after evaporation of the solvents.

EI-CI Analysis: direct introduction (DCI=deposition of sample on filament) Finnigan SSQ7000 mass spectrometer; mass range m/z=29-900; electron energy 70 eV; source temperature 70° C.; CI reactant gas: ammonia; EI=electron impact ionization; CI=chemical ionization.

Electrospray analysis: (positive electrospray: $ES^+$; negative electrospray: $ES^-$)

LC-MS-DAD-ELSD coupling:

MS: Waters-Micromass Platform II; LC: Agilent HP 1100; column Hypersil Gold Thermo C18; 3×50 mm, 2.5 µm; eluent: gradient Water (with 0.1% formic acid)+acetonitrile; UV: DAD ($\lambda$=200-400 nm).

MS: Waters-Micromass ZQ; LC: Agilent HP 1100; column Xbridge Waters C18, 3×50 mm, 2.5 µm; eluent: gradient Water (with 0.1% formic acid)+acetonitrile; UV: $\lambda$=254 nm.

$^1$H NMR spectrum at 400 MHz on a Brüker Avance DRX-400 spectrometer, with the chemical shifts ($\delta$ in ppm)—in d6-dimethyl sulfoxide solvent (DMSO-d6) referenced to 2.50 ppm at a temperature of 303 K.

EXAMPLE 1

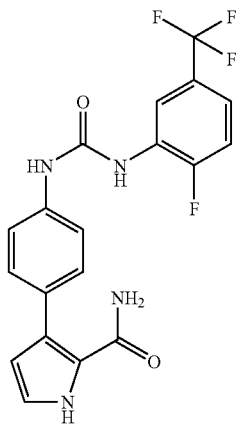

3-{4-[3-(2-Fluoro-5-trifluoromethylphenyl)ureido]
phenyl}-1H-pyrrole-2-carboxamide To 0.490 g (2.435 mmol) of 3-(4-aminophenyl)-1H-pyrrole-2-carboxamide dissolved in 35 cm³ of tetrahydrofuran are added, at a temperature in the region of 20° C. under an argon atmosphere, 0.704 cm³ of 2-fluoro-5-trifluoromethylphenyl isocyanate and 0.678 cm³ of triethylamine. After stirring for 16 hours at a temperature in the region of 20° C., the reaction mixture is concentrated to dryness under reduced pressure (2.7 kPa) to give a residue, which is taken up in 40 cm³ of ethyl acetate. The organic phase is washed with 3 times 20 cm³ of water and 30 cm³ of saturated aqueous sodium chloride solution, dried over anhydrous magnesium sulfate, filtered and concentrated to dryness under reduced pressure (2.7 kPa) to give 1.1 g of a yellow solid, which is purified by flash chromatography [eluent: dichloromethane/methanol/acetonitrile (90/5/5 and then 1/1/0 by volume)]. After concentrating the fractions under reduced pressure, 0.3 g of 3-{4-[3-(2-fluoro-5-trifluoromethylphenyl)ureido]phenyl}-1H-pyrrole-2-carboxamide is obtained in the form of a yellow solid melting at 236° C.; $^1$H NMR (400 MHz, DMSO d6, δ in ppm): 6.15 (t, J=2.5 Hz: 1H); 6.89 (t, J=2.5 Hz: 1H); from 6.10 to 7.30 (very broad mt: 2H); from 7.34 to 7.42 (mt: 3H); from 7.44 to 7.54 (mt: 3H); 8.63 (dd, J=8.5 and 2.5 Hz: 1H); 8.90 (broad d, J=3 Hz: 1H); 9.21 (broad s: 1H); 11.4 (broad s: 1H).

3-(4-Aminophenyl)-1H-pyrrole-2-carboxamide may be Prepared in the Following Manner A suspension of 0.3 g (1.387 mmol) of methyl 3-(4-aminophenyl)-1H-pyrrole-2-carboxylate in 50 cm³ of aqueous 22% ammonia solution is heated in an autoclave at a temperature in the region of 50° C., under 12 bar, for 20 hours. After stopping the heating and then returning to room temperature and pressure, the reaction mixture is concentrated to dryness under reduced pressure (2.7 kPa) to give 0.31 g of an orange-coloured solid, which is purified by flash chromatography [eluent: dichloromethane/methanol/acetonitrile (96/2/2 by volume)]. After concentrating the fractions under reduced pressure, 0.085 g of 3-(4-aminophenyl)-1H-pyrrole-2-carboxamide is obtained in the form of a yellow solid; M.W.=201, IE: m/z=201 M$^+$, m/z=184 [M–NH$_3$]$^+$, m/z=155 [M–H$_2$CONH$_2$]$^+$.

Methyl 3-(4-aminophenyl)-1H-pyrrole-2-carboxylate may be Prepared in the Following Manner To a suspension of 0.1 g (0.942 mmol) of 10% palladium-on-charcoal in 35 cm³ of methanol is added, at a temperature in the region of 20° C., 1 g (4.061 mmol) of methyl 3-(4-nitrophenyl)-1H-pyrrole-2-carboxylate. After hydrogenating for 20 hours in an autoclave under 3 bar of hydrogen, at a temperature in the region of 35° C., the reaction mixture is filtered, the catalyst is rinsed with twice 5 cm³ of methanol and the filtrate is then concentrated to dryness under reduced pressure (2.7 kPa) to give 0.67 g of methyl 3-(4-aminophenyl)-1H-pyrrole-2-carboxylate in the form of an orange-coloured solid; M.W.=216, IE: m/z=216 M$^+$, m/z=184 [M-CH$_3$OH]$^+$, m/z=155 [M–H$_2$COOCH$_3$]$^+$.

Methyl 3-(4-nitrophenyl)-1H-pyrrole-2-carboxylate may be Prepared in the Following Manner To a suspension of 1.62 g (40.63 mmol) of 60% sodium hydride in mineral oil in 100 cm³ of tetrahydrofuran is added dropwise over 25 minutes, at a temperature in the region of 20° C. under an argon atmosphere, a mixture of 5.87 g (19.35 mmol) of 1-[(E)-2-(4-methylphenyl)sulfonylvinyl]-4-nitrobenzene and 3.7 cm³ (38.7 mmol) of methyl isocyanoacetate dissolved in 150 cm³ of tetrahydrofuran. After stirring for 5 hours at a temperature in the region of 20° C., the reaction mixture is taken up in a mixture of 100 cm³ of water and 200 cm³ of ethyl acetate. The organic phase is washed with twice 100 cm³ of water and 150 cm³ of saturated aqueous sodium chloride solution, dried over anhydrous magnesium sulfate, filtered and concentrated to dryness under reduced pressure (2.7 kPa) to give 5.3 g of a brown oil, which is purified by flash chromatography [eluent: dichloromethane]. After concentrating the fractions under reduced pressure, 2.12 g of methyl 3-(4-nitrophenyl)-1H-pyrrole-2-carboxylate are obtained in the form of a yellow solid; M.W.=246, IE: m/z=246 M$^+$, m/z=214 [M-CH$_3$OH]$^+$.

1-[(E)-2-(4-Methylphenyl)sulfonylvinyl]-4-nitrobenzene may be Prepared in the Following Manner To 15 g (85.47 mmol) of methyl p-tolyl sulfone dissolved in 450 cm³ of tetrahydrofuran are added, at a temperature in the region of 0° C. under an argon atmosphere, 117.5 cm³ (188 mmol) of a 1.06 M solution of n-butyl-lithium in hexane. After stirring for 30 minutes at a temperature in the region of 0° C. are added, under an argon atmosphere, 13 cm³ (85.47 mmol) of diethylchlorophosphate dissolved in 70 cm³ of tetrahydrofuran. After stirring for 30 minutes at a temperature in the region of 0° C., the reaction mixture is cooled to a temperature in the region of –78° C., followed by addition, under an argon atmosphere, of 13.05 g (85.47 mmol) of 4-nitrobenzaldehyde dissolved in 130 cm³ of tetrahydrofuran. After stirring for 1 hour at a temperature in the region of –78° C., the temperature of the reaction mixture is allowed to rise to a temperature in the region of 20° C., 100 cm³ of water are added and the mixture is concentrated under reduced pressure (2.7 kPa) to give a beige-coloured solid. The solid is stirred in 250 cm³ of water for 20 minutes, filtered, washed with three times 40 cm³ of water and oven-dried under reduced pressure (2.7 kPa) at 35° C. for 5 hours to give 25.43 g of 1-[(E)-2-(4-methylphenyl)sulfonylvinyl]-4-nitrobenzene in the form of a beige-coloured solid melting at 176° C.; M.W.=303, IE: m/z=303 M+, m/z=239 [M-SO$_2$]$^+$, m/z=139 [CH$_3$-Ph-SO]$^+$.

EXAMPLE 2

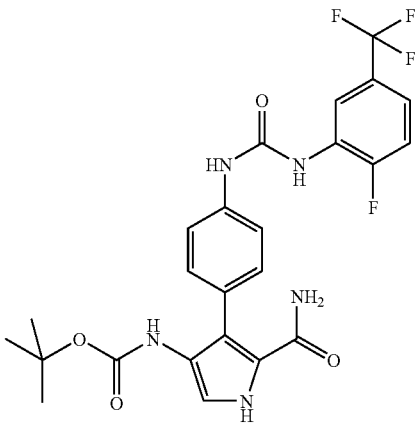

4-tert-Butyloxycarbonylamino-3-{4-[3-(2-fluoro-5-trifluoromethylphenyl)-ureido]phenyl}-1H-pyrrole-2-carboxamide To 0.096 g (0.303 mmol) of 4-tert-butyloxycarbonylamino-3-(4-aminophenyl)-1H-pyrrole-2-carboxamide dissolved in 11 cm³ of tetrahydrofuran is added, at a temperature in the region of 20° C. under an argon atmosphere, 0.044 cm³ of 2-fluoro-5-trifluoromethylphenyl isocyanate. After stirring for 1 hour at a temperature in the region of 20° C., the reaction mixture is diluted with 40 cm³ of ethyl acetate and then washed with three times 15 cm³ of water and 15 cm³ of saturated aqueous sodium chloride solution, dried over anhydrous magnesium sulfate, filtered and concentrated to dryness under reduced pressure (2.7 kPa) to give 0.181 g of a yellow solid, which is purified by flash chromatography [eluent: dichloromethane/methanol/acetonitrile (90/5/5 by volume)]. After concentrating the fractions under reduced pressure, 0.15 g of 4-tert-butyloxycarbonylamino-3-{4-[3-(2-fluoro-5-trifluoromethylphenyl)ureido]phenyl}-1H-pyrrole-2-carboxamide is obtained in the form of a yellow solid; $^1$H NMR (400 MHz, DMSO d6, δ in ppm) 1.35 (broad s, 9H); 5.70 (broad m, 1H); 6.88 (broad s, 1H); 7.05 (broad m, 1H); 7.26 (d, J=8.5 Hz, 2H); 7.39 (m, 1H); 7.49 (partially masked m, 1H); 7.49 (d, J=8.5 Hz, 2H); 7.70 (broad s, 1H); 8.62 (dd, J=2.5 and 7.5 Hz, 1H); 9.03 (broad s, 1H); 9.36 (s, 1H); 11.3 (broad s, 1H):; ES$^+$: m/z=522: [M+H]$^+$; ES$^-$: m/z=520: [M–H]$^-$.

4-tert-Butyloxycarbonylamino-3-(4-aminophenyl)-1H-pyrrole-2-carboxamide may be Prepared in the Following Manner To a suspension of 0.024 g (0.222 mmol) of 10% palladium-on-charcoal in 63 cm³ of methanol is added, at a temperature in the region of 20° C., 0.331 g (0.956 mmol) of 4-tert-butyloxycarbonylamino-3-(4-nitrophenyl)-1H-pyrrole-2-carboxamide. After hydrogenating for 5 hours in an autoclave under 4 bar of hydrogen, at a temperature in the region of 40° C., the reaction mixture is filtered. The catalyst is rinsed with twice 15 cm³ of methanol and the filtrate is then concentrated to dryness under reduced pressure (2.7 kPa) to give 0.3 g of 4-tert-butyloxycarbonylamino-3-(4-aminophenyl)-1H-pyrrole-2-carboxamide in the form of a white solid melting at about 142° C.; EI: m/z=316 M$^+$; m/z=260 [M-tBu]$^+$; m/z=243 [M-OtBu]$^+$; m/z=199 [243-CONH$_2$]$^+$; m/z=57: [tBu]$^+$ base peak.

4-tert-Butyloxycarbonylamino-3-(4-nitrophenyl)-1H-pyrrole-2-carboxamide may be Prepared in the Following Manner To 0.45 g (1.635 mmol) of 5-carbamoyl-4-(4-nitrophenyl)-1H-pyrrole-3-carboxylic acid suspended in 15 cm³ of acetonitrile is added, at a temperature in the region of 5° C. under an argon atmosphere, 0.241 cm³ of triethylamine followed by addition of 0.370 cm³ of diphenoxyphosphoryl azide. The reaction medium is allowed to warm to a temperature in the region of 20° C. over 30 minutes and is then heated at a temperature in the region of 60° C. for 2.5 hours. The reaction mixture is concentrated to dryness under reduced pressure (2.7 kPa) to give a brown oil, which is taken up in 25 cm³ of tert-butanol. After stirring for 2 hours at a temperature in the region of 60° C., the reaction mixture is concentrated to dryness under reduced pressure (2.7 kPa) to give 0.56 g of an ochre-coloured solid, which is purified by flash chromatography [eluent: dichloromethane/methanol/acetonitrile (96/2/2 by volume)]. After concentrating the fractions under reduced pressure, 0.331 g of 4-tert-butyloxycarbonylamino-3-(4-nitrophenyl)-1H-pyrrole-2-carboxamide is obtained in the form of a yellow solid; $^1$H NMR (400 MHz, DMSO d6, δ in ppm):; EI: m/z=346 M$^+$; m/z=290 [M-tBu]$^+$; m/z=273 [M-OtBu]$^+$; m/z=229 [273-CONH$_2$]$^+$; m/z=57 [tBu]$^+$ base peak.

5-Carbamoyl-4-(4-nitrophenyl)-1H-pyrrole-3-carboxylic acid may be prepared in the following manner A solution of 2.8 g (9.232 mmol) of ethyl 5-carbamoyl-4-(4-nitrophenyl)-1H-pyrrole-3-carboxylate in 33.6 cm³ (0.614 mol) of concentrated sulfuric acid is heated at a temperature in the region of 80° C. for 2 hours. The reaction mixture is poured slowly and with stirring into 350 cm³ of ice-water. After stirring for 30 minutes, the reaction mixture is filtered through a No 3 sinter funnel. The solid is washed with 4 times 100 cm³ of ice-water and then dried under reduced pressure (2.7 kPa) at a temperature in the region of 45° C. for 24 hours, to give 2.25 g of 5-carbamoyl-4-(4-nitrophenyl)-1H-pyrrole-3-carboxylic acid in the form of a beige-coloured solid; ES$^+$: m/z=276: [M+H]$^+$; ES$^-$: m/z=274: [M–H]$^-$.

Ethyl 5-carbamoyl-4-(4-nitrophenyl)-1H-pyrrole-3-carboxylate may be Prepared in the Following Manner To 18 g (69.16 mmol) of ethyl 4-(4-nitrophenyl)-1H-pyrrole-3-carboxylate suspended in 300 cm³ of dichloromethane are added, at a temperature in the region of –24° C. under an argon atmosphere, 8.1 cm³ (91.29 mmol) of chlorosulfonyl isocyanate dissolved in 100 cm³ of dichloromethane. After stirring for 30 minutes at a temperature in the region of –24° C., the reaction medium is allowed to warm to a temperature in the region of 20° C. over 2 hours. After initiating the crystallization using a glass rod, the reaction mixture is stirred at a temperature in the region of 20° C. for 30 minutes. The reaction mixture is then cooled to a temperature in the region of 5° C. and then filtered through a No 3 sinter funnel. The solid is washed with three times 40 cm³ of dichloromethane and then dried under reduced pressure (2.7 kPa) at a temperature in the region of 40° C. for 3 hours. The solid is then suspended in 500 cm³ of water; the resulting mixture is then heated at a temperature in the region of 40° C. for 3 hours and then cooled at a temperature in the region of 5° C. for 1 hour before filtering through a No 3 sinter funnel. The solid is successively washed with twice 50 cm³ of water and twice 30 cm³ of petroleum ether and then dried under reduced pressure (2.7 kPa) at a temperature in the region of 40° C. for 16 hours to give 15.4 g of ethyl 5-carbamoyl-4-(4-nitrophenyl)-1H-pyrrole-3-carboxylate in the form of a beige-coloured solid; EI: m/z=303: M⁺; m/z=274 [M-CH₂CH₃]⁺; m/z=258 [M-OCH₂CH₃]⁺; m/z=241 [258-OH]⁺ base peak.

Ethyl 4-(4-nitrophenyl)-1H-pyrrole-3-carboxylate may be prepared in the following manner To a suspension of 0.512 g (12.8 mmol) of 60% sodium hydride in mineral oil in 20 cm³ of diethyl ether is added dropwise, at a temperature in the region of 20° C. under an argon atmosphere, a mixture of 2.212 g (10 mmol) of ethyl 4-nitrocinnamate and 1.991 g (10.2 mmol) of tosylmethyl isocyanate dissolved in a mixture of 18 cm³ of dimethyl sulfoxide and 36 cm³ of diethyl ether. After stirring for 1 hour at reflux, the reaction mixture is taken up in a mixture of 70 cm³ of water, 20 cm³ of saturated aqueous sodium chloride solution and 100 cm³ of ethyl acetate. The organic phase is extracted with 50 cm³ of diethyl ether and twice 75 cm³ of dichloromethane. All the organic phases are combined, dried over anhydrous sodium sulfate, filtered and concentrated to dryness under reduced pressure (2.7 kPa) to give a black oil, which is taken up in a mixture of 75 cm³ of water and 50 cm³ of ethyl acetate. The aqueous phase is extracted with twice 50 cm³ of ethyl acetate. All the organic phases are combined, dried over anhydrous sodium sulfate, filtered and concentrated to dryness under reduced pressure (2.7 kPa) to give 2.82 g of a black solid, which is purified by flash chromatography [eluent: cyclohexane/ethyl acetate (3/2 by volume)]. After concentrating the fractions under reduced pressure, 1.48 g of an orange-coloured solid are obtained, which product is purified by flash chromatography [eluent: dichloromethane]. After concentrating the fractions under reduced pressure, 0.78 g of ethyl 4-(4-nitrophenyl)-1H-pyrrole-3-carboxylate is obtained in the form of a yellow solid; IE: m/z=260 (M⁺) base peak, m/z=215 (M-C₂H₅O⁺), m/z=169 (215-NO₂).

EXAMPLE 3

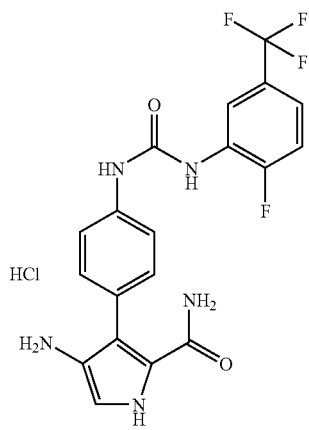

4-Amino-3-{4-[3-(2-fluoro-5-trifluoromethylphenyl)ureido]phenyl}-1H-pyrrole-2-carboxamide hydrochloride To 0.15 g (0.288 mmol) of 4-tert-butyloxycarbonylamino-3-{4-[3-(2-fluoro-5-trifluoromethylphenyl)ureido]phenyl}-1H-pyrrole-2-carboxamide suspended in 1 cm³ of dioxane is added, at a temperature in the region of 20° C., 0.72 cm³ of a 4N solution of hydrogen chloride in dioxane. After stirring for 5 hours at a temperature in the region of 20° C., the reaction mixture is concentrated to dryness under reduced pressure (2.7 kPa) to give a residue, which is purified by flash chromatography [eluent: dichloromethane/methanol/acetonitrile (gradient of from 90/5/5 to 80/10/10 by volume)]. After concentrating the fractions under reduced pressure, 85 mg of a yellow solid are obtained, and are then stirred in 4 cm³ of pentane for 16 hours. After filtering through a No 3 sinter funnel, the solid is washed with twice 1 cm³ of pentane and then dried under reduced pressure (2.7 kPa) at a temperature in the region of 40° C. for 4 hours to give 47 mg of 4-amino-3-{4-[3-(2-fluoro-5-trifluoromethylphenyl)ureido]phenyl}-1H-pyrrole-2-carboxamide hydrochloride in the form of a yellow solid melting at about 174° C.; ¹H NMR (400 MHz, DMSO d6, δ in ppm) from 5.30 to 8.00 (very broad m, 2H); 6.34 (d, J=2.5 Hz, 1H); 7.27 (d, J=8.5 Hz, 2H); 7.39 (m, 1H); 7.50 (partially masked m, 1H); 7.53 (d, J=8.5 Hz, 2H); 8.63 (broad d, J=7.0 Hz, 1H); 8.96 (broad s, 1H); 9.29 (s, 1H); 10.7 (broad s, 1H):; ES⁺: m/z=422: [M+H]⁺; ES⁻: m/z=420: [M−H]⁻.

4-tert-Butyloxycarbonylamino-3-{4-[3-(2-fluoro-5-trifluoromethylphenyl)-ureido]phenyl}-1H-pyrrole-2-carboxamide may be Prepared as Described in Example 2

EXAMPLE 4

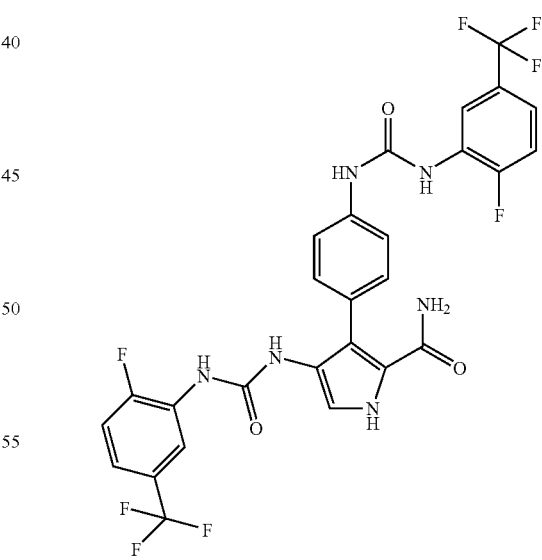

4-[3-(2-Fluoro-5-trifluoromethylphenyl)ureido]-3-{4-[3-(2-fluoro-5-trifluoro-methylphenyl)ureido]phenyl}-1H-pyrrole-2-carboxamide To 0.107 g (0.254 mmol) of 4-amino-3-{4-[3-(2-fluoro-5-trifluoromethyl-phenyl)ureido]phenyl}-1H-pyrrole-2-carboxamide hydrochloride dissolved in 10 cm³ of tetrahydrofuran are added, at a temperature in the region of 20° C. under an argon atmosphere, 0.037 cm³ of 2-fluoro-5-trifluoromethylphenyl isocyanate and 0.035 cm³ of triethylamine. After stirring for 1 hour at a temperature in the region of 20° C., the reaction mixture is diluted with 10 cm³ of ethyl acetate and then washed successively with twice 15 cm³ of water and 15 cm³ of saturated aqueous sodium chloride solution, dried over anhydrous magnesium sulfate, filtered and concentrated to dryness under reduced pressure (2.7 kPa) to give 0.27 g of a yellow solid, which is purified by flash chromatography [eluent: cyclohexane/ethyl acetate (7/3 by volume) and then dichloromethane/methanol/acetonitrile (90/5/5 by volume)]. After concentrating the fractions under reduced pressure, 0.079 g of 4-[3-(2-fluoro-5-trifluoromethylphenyl)ureido]-3-{4-[3-(2-fluoro-5-trifluoromethylphenyl)-ureido]phenyl}-1H-pyrrole-2-carboxamide is obtained in the form of a white solid melting at between 186 and 190° C.; ¹H NMR (400 MHz, DMSO d6, δ in ppm) 5.62 (very broad m, 1H); 7.02 (very broad m, 1H); 7.24 (d, J=3.0 Hz, 1H); 7.30 (d, J=8.5 Hz, 2H); 7.32 (partially masked m, 1H); 7.39 (m, 1H); 7.42 (dd, J=8.5 and 11.5 Hz, 1H); 7.51 (dd, J=8.5 and 11.5 Hz, 1H); 7.61 (d, J=8.5 Hz, 2H); 8.05 (s, 1H); 8.64 (m, 2H); 9.06 (broad s, 1H); 9.12 (broad s, 1H); 9.45 (broad s, 1H); 11.3 (broad s, 1H);:; ES⁺: m/z=627: [M+H]⁺.

4-Amino-3-{4-[3-(2-fluoro-5-trifluoromethylphenyl)ureido]phenyl}-1H-pyrrole-2-carboxamide hydrochloride may be prepared as described in Example 3

EXAMPLE 5

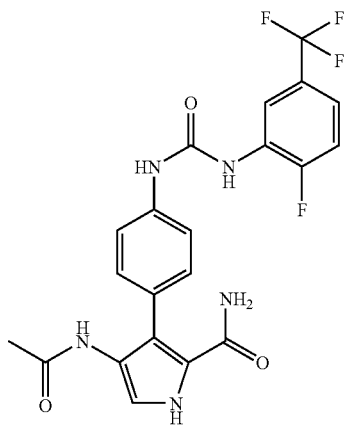

4-Acetylamino-3-{4-[3-(2-fluoro-5-trifluoromethylphenyl)ureido]phenyl}-1H-pyrrole-2-carboxamide To 0.15 g (0.328 mmol) of 4-amino-3-{4-[3-(2-fluoro-5-trifluoromethylphenyl)-ureido]phenyl}-1H-pyrrole-2-carboxamide hydrochloride dissolved in 4.5 cm³ of tetrahydrofuran are added, at a temperature in the region of 20° C. under an argon atmosphere, 0.023 cm³ of acetyl chloride, 0.091 cm³ of triethylamine and 8 mg of 4-dimethylaminopyridine. After stirring for 16 hours at a temperature in the region of 20° C., the reaction mixture is diluted with 15 cm³ of dichloromethane and then washed with twice 10 cm³ of saturated aqueous sodium chloride solution, dried over anhydrous magnesium sulfate, filtered and concentrated to dryness under reduced pressure (2.7 kPa) to give a solid, which is recrystallized while hot from 5 cm³ of dichloromethane. The recrystallized solid is filtered off through a No 3 sinter funnel, washed with twice 3 cm³ of dichloromethane and then dried under reduced pressure (2.7 kPa) at a temperature in the region of 40° C. for 5 hours to give 0.084 g of 4-acetylamino-3-{4-[3-(2-fluoro-5-trifluoromethylphenyl)ureido]phenyl}-1H-pyrrole-2-carboxamide in the form of a white solid melting at 228.5° C.; ES⁺: m/z=464: [M+H]⁺.

¹H NMR (400 MHz, DMSO d6, δ in ppm) 1.87 (s, 3H); 5.62 (broad m, 1H); 7.03 (broad m, 1H); 7.10 (d, J=3.0 Hz, 1H); 7.25 (d, J=8.5 Hz, 2H); 7.39 (m, 1H); 7.50 (partially masked m, 1H); 7.54 (d, J=8.5 Hz, 2H); 8.62 (dd, J=2.5 and 7.5 Hz, 1H); 8.70 (s, 1H); 9.02 (broad s, 1H); 9.36 (broad s, 1H); 11.3 (broad s, 1H);

4-Amino-3-{4-[3-(2-fluoro-5-trifluoromethylphenyl)ureido]phenyl}-1H-pyrrole-2-carboxamide hydrochloride may be Prepared as Described in Example 3

EXAMPLE 6

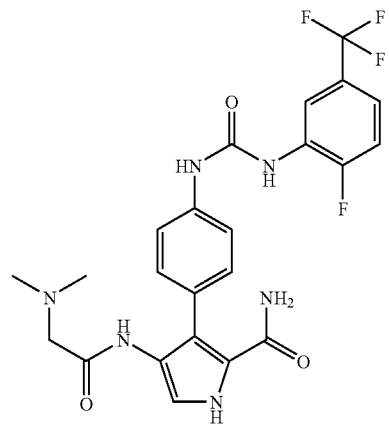

4-(2-Dimethylaminoacetylamino)-3-{4-[3-(2-fluoro-5-trifluoromethylphenyl)-ureido]phenyl}-1H-pyrrole-2-carboxamide To 0.15 g (0.328 mmol) of 4-amino-3-{4-[3-(2-fluoro-5-trifluoromethylphenyl)-ureido]phenyl}-1H-pyrrole-2-carboxamide hydrochloride dissolved in 4.5 cm³ of tetrahydrofuran are added, at a temperature in the region of 20° C. under an argon atmosphere, 0.052 g of dimethylaminoacetyl chloride hydrochloride, 0.091 cm³ of triethylamine and 8 mg of 4-dimethylaminopyridine. After stirring for 16 hours at a temperature in the region of 20° C., the reaction mixture is diluted with 15 cm³ of dichloromethane and then washed with twice 10 cm³ of saturated aqueous sodium chloride solution, dried over anhydrous magnesium sulfate, filtered and concentrated to dryness under reduced pressure (2.7 kPa) to give 148 mg of a beige-coloured solid, which is purified by flash chromatography [eluent: dichloromethane/methanol/acetonitrile (82/9/9 by volume)]. After concentrating the fractions under reduced pressure, 0.107 g of 4-(2-dimethylaminoacetylamino)-3-{4-[3-(2-fluoro-5-trifluoromethylphenyl)ureido]phenyl}-1H-pyrrole-2-carboxamide is obtained in the form of a yellow solid melting at 178° C.; ES⁺: m/z=507: [M+H]⁺.

¹H NMR (400 MHz, DMSO d6, δ in ppm) 2.14 (s, 6H); 2.91 (s, 2H); 5.79 (broad m, 1H); 7.06 (broad m, 1H); from 7.25 to 7.31 (m, 3H); 7.39 (m, 1H); 7.50 (m, 1H); 7.58 (d, J=8.5 Hz, 2H); 8.61 (m, 1H); 8.68 (s, 1H); 9.11 (broad s, 1H); 9.49 (broad s, 1H); 11.35 (broad s, 1H);

4-Amino-3-{4-[3-(2-fluoro-5-trifluoromethylphenyl)ureido]phenyl}-1H-pyrrole-2-carboxamide hydrochloride may be Prepared as Described in Example 3

EXAMPLE 7

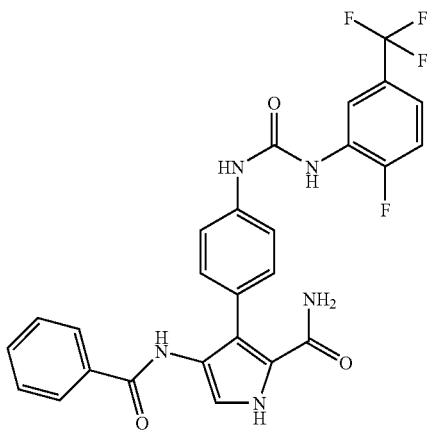

4-Benzoylamino-3-{4-[3-(2-fluoro-5-trifluoromethylphenyl)ureido]phenyl}-1H-pyrrole-2-carboxamide To 0.15 g (0.328 mmol) of 4-amino-3-{4-[3-(2-fluoro-5-trifluoromethyl-phenyl)ureido]phenyl}-1H-pyrrole-2-carboxamide hydrochloride dissolved in 4.5 cm³ of tetrahydrofuran are added, at a temperature in the region of 20° C. under an argon atmosphere, 0.038 cm³ of benzoyl chloride and 0.091 cm³ of triethylamine. After stirring for 4 hours at a temperature in the region of 20° C., the reaction mixture is diluted with 15 cm³ of dichloromethane and then washed with twice 10 cm³ of saturated aqueous sodium chloride solution, dried over anhydrous magnesium sulfate, filtered and concentrated under reduced pressure (2.7 kPa) to give a solid, which is recrystallized while hot in 5 cm³ of methanol. The recrystallized solid is filtered through a No 3 sinter funnel, washed with twice 2 cm³ of methanol and then dried under reduced pressure (2.7 kPa) at a temperature in the region of 35° C. for 5 hours to give 0.075 g of 4-benzoylamino-3-{4-[3-(2-fluoro-5-trifluoromethylphenyl)-ureido]phenyl}-1H-pyrrole-2-carboxamide in the form of a white solid melting at 239.7° C.; ES⁺: m/z=526: [M+H]⁺.

4-Amino-3-{4-[3-(2-fluoro-5-trifluoromethylphenyl)ureido]phenyl}-1H-pyrrole-2-carboxamide hydrochloride may be Prepared as Described in Example 3

EXAMPLE 8

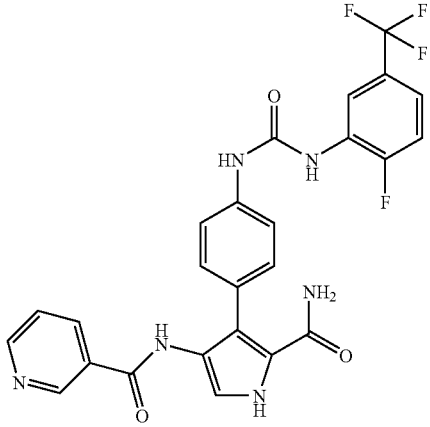

4-Nicotinoylamino-3-{4-[3-(2-fluoro-5-trifluoromethylphenyl)ureido]phenyl}-1H-pyrrole-2-carboxamide To 0.15 g (0.328 mmol) 4-amino-3-{4-[3-(2-fluoro-5-trifluoromethylphenyl)-ureido]phenyl}-1H-pyrrole-2-carboxamide hydrochloride dissolved in 4.5 cm³ of tetrahydrofuran are added, at a temperature in the region of 20° C. under an argon atmosphere, 0.058 g of nicotinoyl chloride hydrochloride, 0.091 cm³ of triethylamine and 8 mg of 4-dimethylaminopyridine. After stirring for 16 hours at reflux, the reaction mixture is diluted with 15 cm³ of dichloromethane and then washed with twice 10 cm³ of saturated aqueous sodium chloride solution, dried over anhydrous magnesium sulfate, filtered and concentrated to dryness under reduced pressure (2.7 kPa) to give 148 mg of a beige-coloured solid, which is purified by flash chromatography [eluent: dichloromethane/methanol/acetonitrile (82/9/9 by volume)]. After concentrating the fractions under reduced pressure, 0.01 g of 4-nicotinoyl-amino-3-{4-[3-(2-fluoro-5-trifluoromethylphenyl)ureido]phenyl}-1H-pyrrole-2-carboxamide is obtained in the form of a yellow solid; ES⁺: m/z=527: [M+H]⁺.

4-Amino-3-{4-[3-(2-fluoro-5-trifluoromethylphenyl)ureido]phenyl}-1H-pyrrole-2-carboxamide hydrochloride may be Prepared as Described in Example 3

EXAMPLE 9

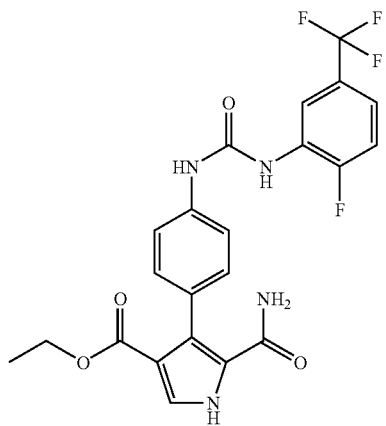

Ethyl 5-carbamoyl-4-{4-[3-(2-fluoro-5-trifluoromethylphenyl)ureido]phenyl}-1H-pyrrole-3-carboxylate To 0.23 g (0.842 mmol) of ethyl 5-carbamoyl-4-(4-aminophenyl)-1H-pyrrole-3-carboxylate dissolved in 30 cm³ of tetrahydrofuran is added, at a temperature in the region of 20° C. under an argon atmosphere, 0.122 cm³ (0.842 mmol) of 2-fluoro-5-trifluoromethylphenyl isocyanate. After stirring for 2 hours at a temperature in the region of 20° C., the reaction mixture is diluted with 40 cm³ of ethyl acetate and then washed successively with twice 30 cm³ of water and 30 cm³ of saturated aqueous sodium chloride solution, dried over anhydrous magnesium sulfate, filtered and concentrated to dryness under reduced pressure (2.7 kPa) to give 0.431 g of a yellow solid, which is purified by flash chromatography [eluent: dichloromethane/methanol/acetonitrile (94/3/3 by volume)]. After concentrating the fractions under reduced pressure, 0.345 g of a yellow solid is obtained, which is then stirred in 5 cm³ of dichloromethane for 1 hour. After filtering through a No. 3 sinter funnel, the solid is washed with twice 3 cm³ of dichloromethane and then dried under reduced pressure (2.7 kPa) at a temperature in the region of 30° C. for 4 hours to give 0.333 g of ethyl 5-carbamoyl-4-{4-[3-(2-fluoro-5-trifluoromethylphenyl)ureido]phenyl}-1H-pyrrole-3-carboxylate in the form of a yellow solid melting at 179° C.; ¹H NMR (400 MHz, DMSO d6, δ in ppm) 1.05 (t, J=7.0 Hz, 3H); 3.99 (q, J=7.0 Hz, 2H); 5.45 (broad m, 1H); 7.22 (d, J=8.5 Hz, 2H); 7.25 (partially masked m, 1H); 7.39 (m, 1H); 7.47 (s, 1H); 7.49 (partially masked m, 1H); 7.51 (d, J=8.5 Hz, 2H); 8.62 (dd, J=2.5 and 7.5 Hz, 1H); 9.01 (broad s, 1H); 9.36 (s, 1H); 12.1 (broad s, 1H):; ES⁺: m/z=479: [M+H]⁺; ES⁻: m/z=477: [M−H]⁻.

Ethyl 5-carbamoyl-4-(4-aminophenyl)-1H-pyrrole-3-carboxylate may be Prepared in the Following Manner To a suspension of 0.204 g (1.912 mmol) of 10% palladium-on-charcoal in 140 cm³ of methanol are added, at a temperature in the region of 20° C., 2.5 g (8.243 mmol) of ethyl 5-carbamoyl-4-(4-nitrophenyl)-1H-pyrrole-3-carboxylate. After hydrogenating for 4 hours in an autoclave under 4 bar of hydrogen, at a temperature in the region of 35° C., the reaction mixture is filtered; the catalyst is then rinsed with twice 20 cm³ of methanol and the filtrate is then concentrated to dryness under reduced pressure (2.7 kPa) to give a residue, which is used a second time in a hydrogenation reaction under the same conditions as above. After a work-up similar to that described above, 1.93 g of ethyl 5-carbamoyl-4-(4-aminophenyl)-1H-pyrrole-3-carboxylate are thus obtained in the form of a yellow solid; EI: m/z=273: M⁺ base peak; m/z=256 [M−NH₃]⁺; m/z=228 [M−CONH₃]⁺.

Ethyl 5-carbamoyl-4-(4-nitrophenyl)-1H-pyrrole-3-carboxylate may be Prepared as Described in Example 2

The products of Examples 10 to 37 may be prepared by analogy with Example 9, starting with ethyl 5-carbamoyl-4-(4-aminophenyl)-1H-pyrrole-3-carboxylate and the corresponding aryl isocyanate:

EXAMPLE 10

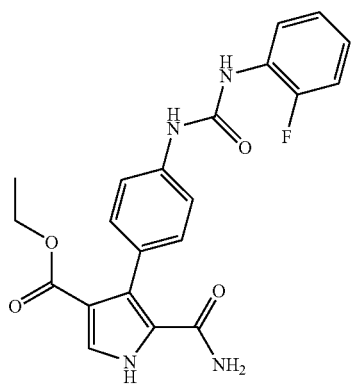

Ethyl 5-carbamoyl-4-{4-[3-(2-fluorophenyl)ureido]phenyl}-1H-pyrrole-3-carboxylate ES⁺: m/z=411 [M+H]⁺.

EXAMPLE 11

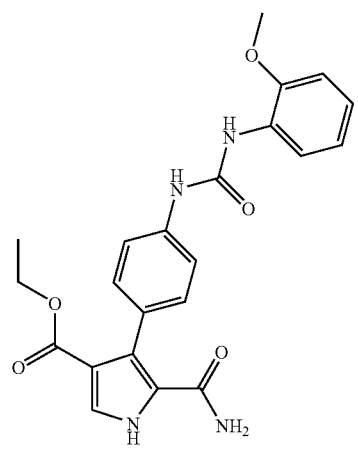

Ethyl 5-carbamoyl-4-{4-[3-(2-methoxyphenyl)ureido]phenyl}-1H-pyrrole-3-carboxylate ES⁺: m/z=423 [M+H]⁺.

EXAMPLE 12

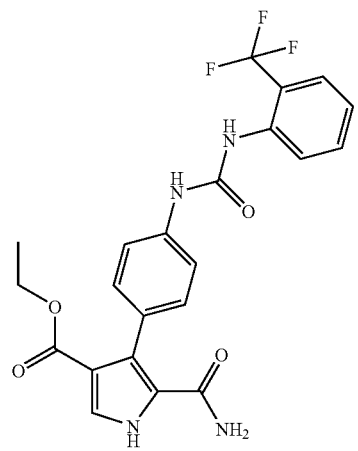

Ethyl 5-carbamoyl-4-{4-[3-(2-trifluoromethylphenyl)ureido]phenyl}-1H-pyrrole-3-carboxylate ES⁺: m/z=461 [M+H]⁺.

EXAMPLE 13

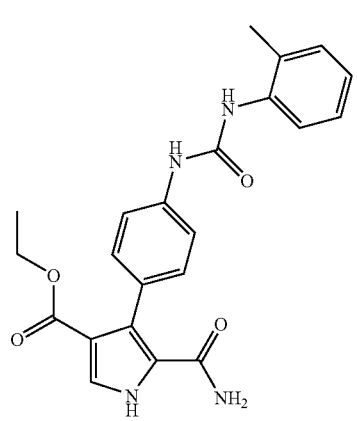

Ethyl 5-carbamoyl-4-[4-(3-o-tolylureido)phenyl]-1H-pyrrole-3-carboxylate

ES⁺: m/z=407 [M+H]⁺.

EXAMPLE 14

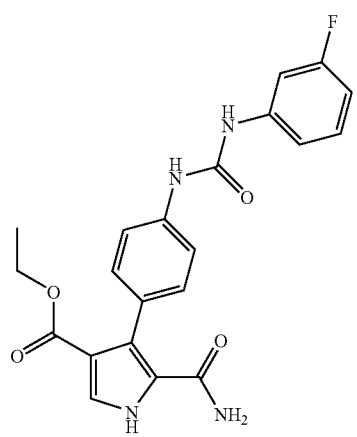

Ethyl 5-carbamoyl-4-{4-[3-(3-fluorophenyl)ureido]phenyl}-1H-pyrrole-3-carboxylate ES⁺: m/z=411 [M+H]⁺.

EXAMPLE 15

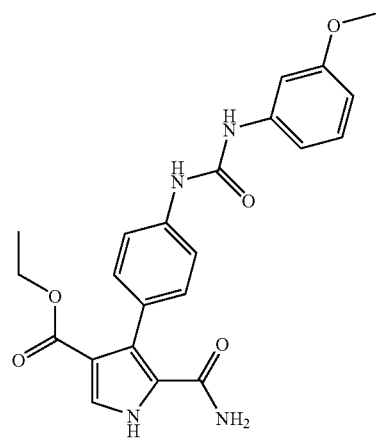

Ethyl 5-carbamoyl-4-{4-[3-(3-methoxyphenyl)ureido]phenyl}-1H-pyrrole-3-carboxylate ES⁺: m/z=423 [M+H]⁺.

EXAMPLE 16

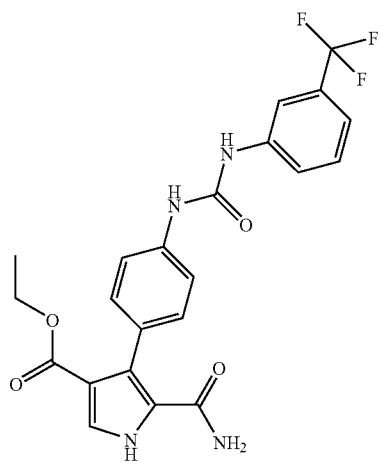

35

Ethyl 5-carbamoyl-4-{4-[3-(3-trifluoromethylphenyl)ureido]phenyl}-1H-pyrrole-3-carboxylate ES⁺: m/z=461 [M+H]⁺.

EXAMPLE 17

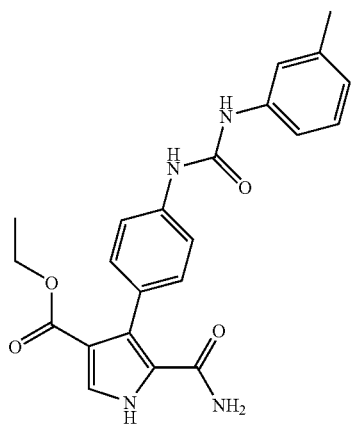

Ethyl 5-carbamoyl-4-[4-(3-m-tolylureido)phenyl]-1H-pyrrole-3-carboxylate

ES⁺: m/z=407 [M+H]⁺.

EXAMPLE 18

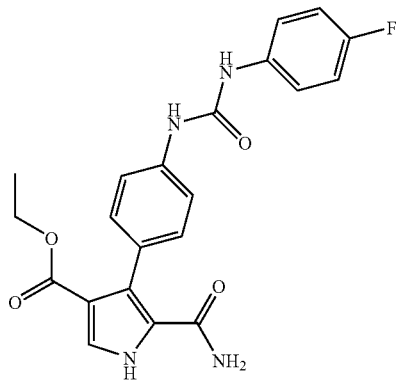

36

Ethyl 5-carbamoyl-4-{4-[3-(4-fluorophenyl)ureido]phenyl}-1H-pyrrole-3-carboxylate ES⁺: m/z=411 [M+H]⁺.

EXAMPLE 19

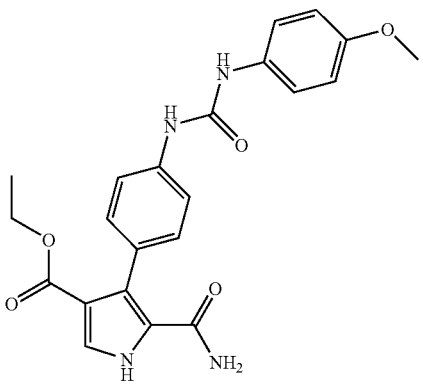

Ethyl 5-carbamoyl-4-{4-[3-(4-methoxyphenyl)ureido]phenyl}-1H-pyrrole-3-carboxylate ES⁺: m/z=423 [M+H]⁺.

EXAMPLE 20

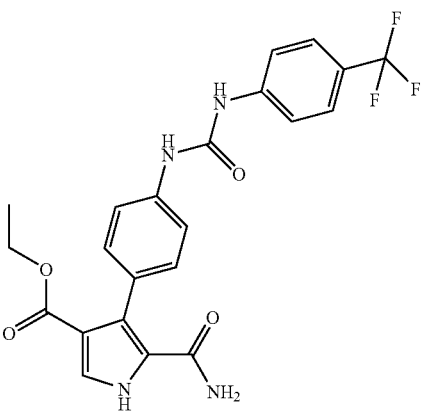

Ethyl 5-carbamoyl-4-{4-[3-(4-trifluoromethylphenyl)ureido]phenyl}-1H-pyrrole-3-carboxylate ES+: m/z=461 [M+H]+.

EXAMPLE 21

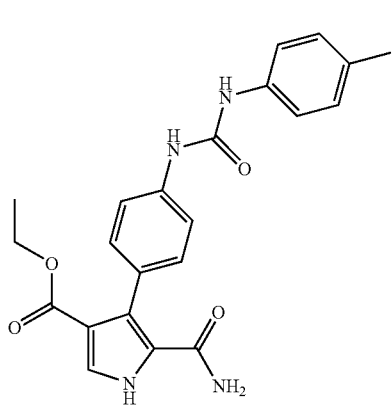

Ethyl 5-carbamoyl-4-[4-(3-p-tolylureido)phenyl]-1H-pyrrole-3-carboxylate

ES+: m/z=407 [M+H]+.

EXAMPLE 22

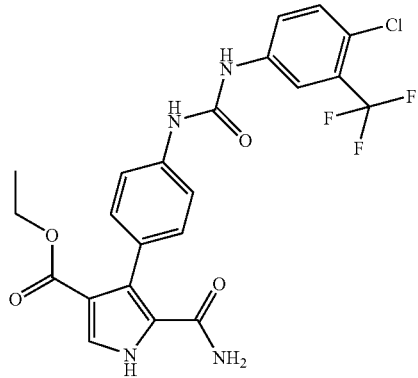

Ethyl 5-carbamoyl-4-{4-[3-(4-chloro-3-trifluoromethylphenyl)ureido]phenyl}-1H-pyrrole-3-carboxylate ES+: m/z=495 [M+H]+.

EXAMPLE 23

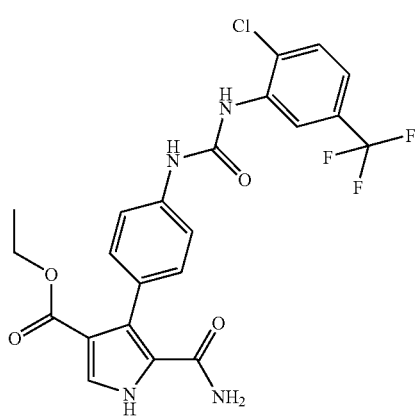

Ethyl 5-carbamoyl-4-{4-[3-(2-chloro-5-trifluoromethylphenyl)ureido]phenyl}-1H-pyrrole-3-carboxylate ES+: m/z=495 [M+H]+.

EXAMPLE 24

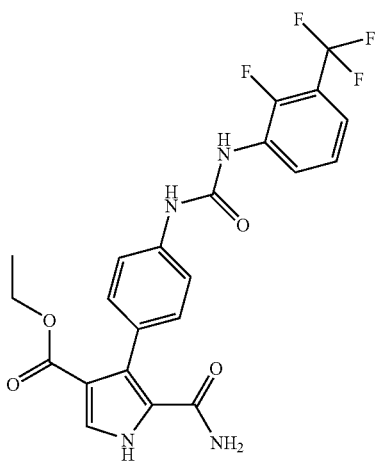

Ethyl 5-carbamoyl-4-{4-[3-(2-fluoro-3-trifluoromethylphenyl)ureido]phenyl}-1H-pyrrole-3-carboxylate ES+: m/z=479 [M+H]+.

EXAMPLE 25

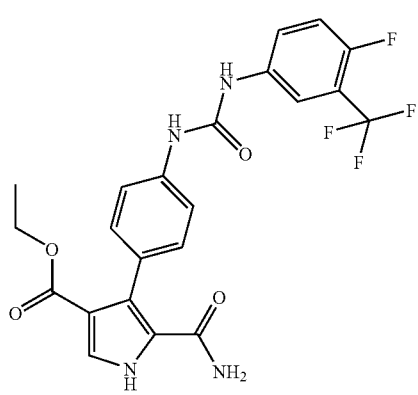

Ethyl 5-carbamoyl-4-{4-[3-(4-fluoro-3-trifluoromethylphenyl)ureido]phenyl}-1H-pyrrole-3-carboxylate ES+: m/z=479 [M+H]+.

EXAMPLE 26

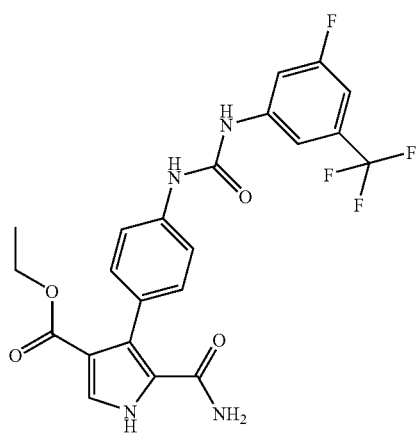

Ethyl 5-carbamoyl-4-{4-[3-(3-fluoro-5-trifluoromethylphenyl)ureido]phenyl}-1H-pyrrole-3-carboxylate ES+: m/z=479 [M+H]+.

EXAMPLE 27

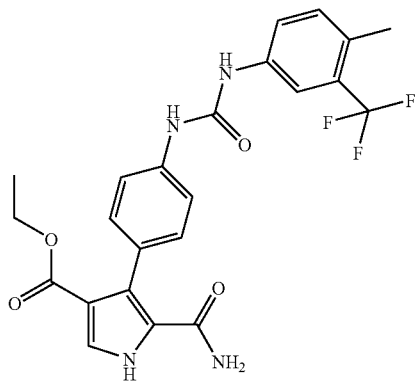

Ethyl 5-carbamoyl-4-{4-[3-(4-methyl-3-trifluoromethylphenyl)ureido]phenyl}-1H-pyrrole-3-carboxylate ES+: m/z=475 [M+H]+.

EXAMPLE 28

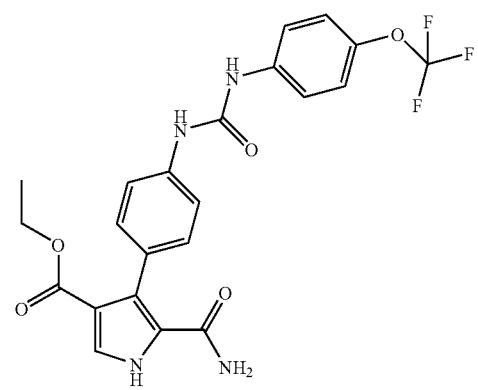

41

Ethyl 5-carbamoyl-4-{4-[3-(4-trifluoromethoxyphenyl)ureido]phenyl}-1H-pyrrole-3-carboxylate ES$^+$: m/z=477 [M+H]$^+$.

EXAMPLE 29

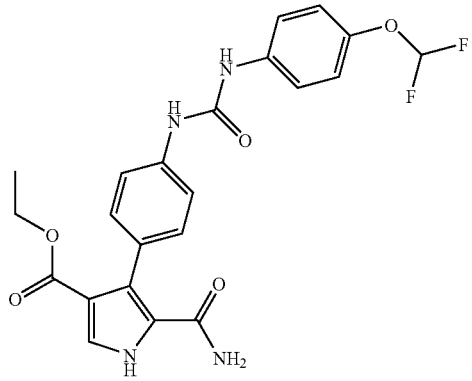

Ethyl 5-carbamoyl-4-{4-[3-(4-difluoromethoxyphenyl)ureido]phenyl}-1H-pyrrole-3-carboxylate ES$^+$: m/z=459 [M+H]$^+$.

EXAMPLE 30

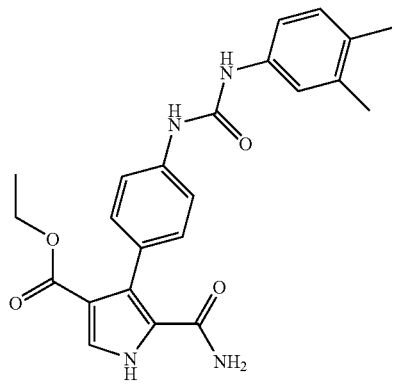

42

Ethyl 5-carbamoyl-4-{4-[3-(3,4-dimethylphenyl)ureido]phenyl}-1H-pyrrole-3-carboxylate ES$^+$: m/z=421 [M+H]$^+$.

EXAMPLE 31

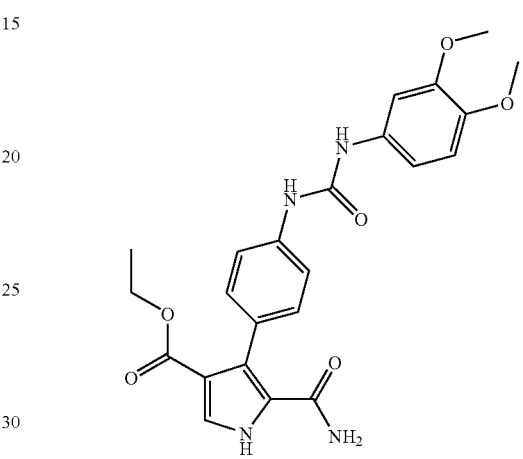

Ethyl 5-carbamoyl-4-{4-[3-(3,4-dimethoxyphenyl)ureido]phenyl}-1H-pyrrole-3-carboxylate ES$^+$: m/z=453 [M+H]$^+$.

EXAMPLE 32

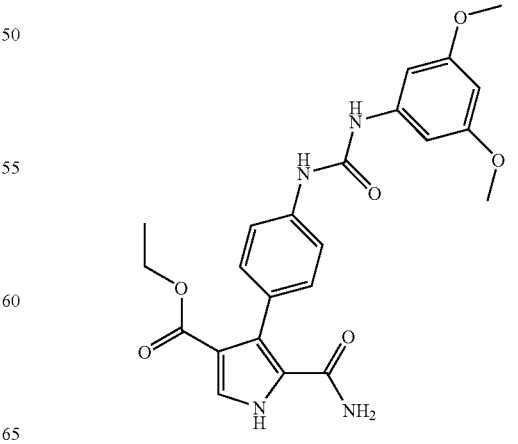

Ethyl 5-carbamoyl-4-{4-[3-(3,5-dimethoxyphenyl)ureido]phenyl}-1H-pyrrole-3-carboxylate ES⁺: m/z=453 [M+H]⁺.

EXAMPLE 33

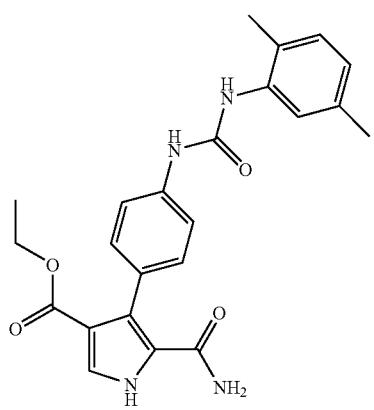

Ethyl 5-carbamoyl-4-{4-[3-(2,5-dimethylphenyl)ureido]phenyl}-1H-pyrrole-3-carboxylate ES⁺: m/z=421 [M+H]⁺.

EXAMPLE 34

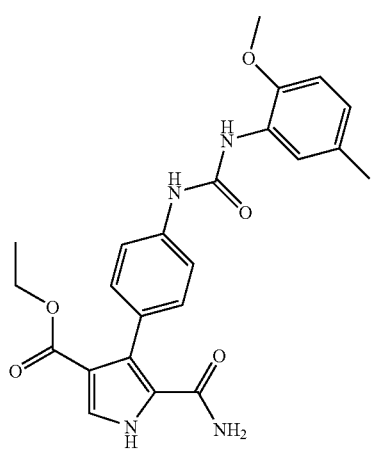

Ethyl 5-carbamoyl-4-{4-[3-(2-methoxy-5-methylphenyl)ureido]phenyl}-1H-pyrrole-3-carboxylate ES⁺: m/z=437 [M+H]⁺.

EXAMPLE 35

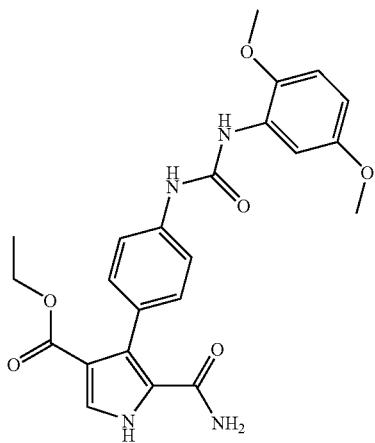

Ethyl 5-carbamoyl-4-{4-[3-(2,5-dimethoxyphenyl)ureido]phenyl}-1H-pyrrole-3-carboxylate ES⁺: m/z=453 [M+H]⁺.

EXAMPLE 36

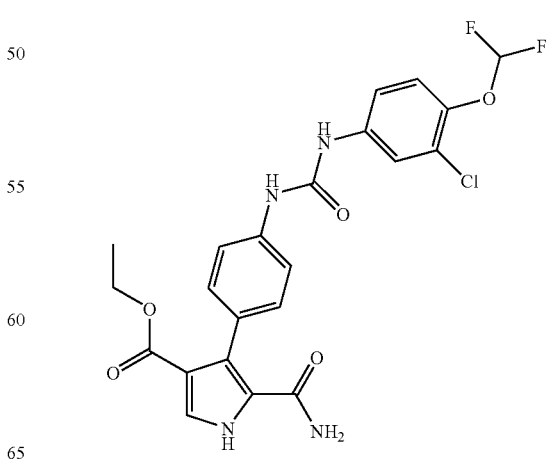

Ethyl 5-carbamoyl-4-{4-[3-(3-chloro-4-difluoromethoxyphenyl)ureido]phenyl}-1H-pyrrole-3-carboxylate ES+: m/z=493 [M+H]+.

EXAMPLE 37

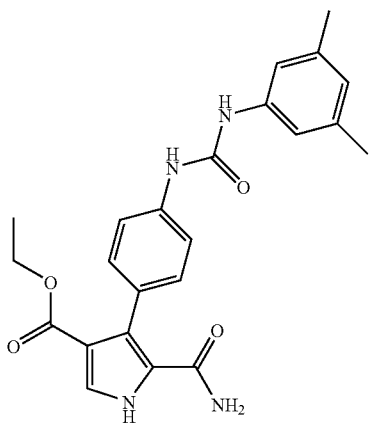

Ethyl 5-carbamoyl-4-{4-[3-(3,5-dimethylphenyl)ureido]phenyl}-1H-pyrrole-3-carboxylate ES+: m/z=421 [M+H]+.

EXAMPLE 38

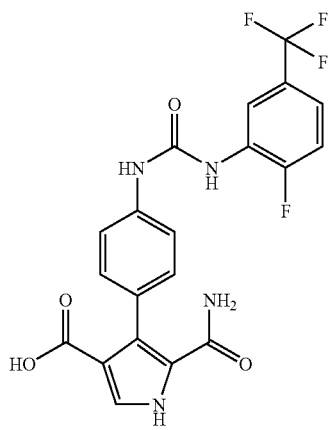

5-Carbamoyl-4-{4-[3-(2-fluoro-5-trifluoromethylphenyl)ureido]phenyl}-1H-pyrrole-3-carboxylic acid To 0.14 g (0.497 mmol) of 5-carbamoyl-4-(4-aminophenyl)-1H-pyrrole-3-carboxylic acid hydrochloride dissolved in 18 cm³ of tetrahydrofuran are added, at a temperature in the region of 20° C. under an argon atmosphere, 0.072 cm³ (0.497 mmol) of 2-fluoro-5-trifluoromethylphenyl isocyanate and 0.07 cm³ (0.497 mmol) of triethylamine. After stirring for 5 hours at a temperature in the region of 20° C., the reaction mixture is concentrated to dryness under reduced pressure (2.7 kPa) to give a residue, which is purified by flash chromatography [eluent: dichloromethane/methanol/acetonitrile (gradient of from 90/5/5 to 80/10/10 by volume)]. After concentrating the fractions under reduced pressure, a solid is obtained, which is then stirred in 5 cm³ of pentane for 3 hours. After filtering through a No. 3 sinter funnel, the solid is washed with twice 1 cm³ of pentane and then dried under reduced pressure (2.7 kPa) at a temperature in the region of 30° C. for 15 hours to give 0.105 g of 5-carbamoyl-4-{4-[3-(2-fluoro-5-trifluoromethylphenyl)ureido]-phenyl}-1H-pyrrole-3-carboxylic acid in the form of a yellow solid melting at 194° C.; ¹H NMR (400 MHz, DMSO d6, δ in ppm): 5.37 (broad m, 1H); 7.23 (d, J=8.5 Hz, 2H); 7.23 (masked m, 1H); 7.39 (m, 1H); 7.42 (d, J=3.0 Hz, 1H); 7.49 (d, J=8.5 Hz, 2H); 7.50 (partially masked m, 1H); 8.64 (dd, J=2.5 and 7.5 Hz, 1H); 8.97 (d, J=2.0 Hz, 1H); 9.35 (s, 1H); 11.6 (broad m, 1H); 12.05 (broad s, 1H); ES+: m/z=451: [M+H]+; ES−: m/z=449: [M−H]−.

5-Carbamoyl-4-(4-aminophenyl)-1H-pyrrole-3-carboxylic acid hydrochloride may be Prepared in the Following Manner To a suspension of 0.135 g (0.126 mmol) of 10% palladium-on-charcoal in 20 cm³ of methanol is added, at a temperature in the region of 20° C., 0.15 g (0.545 mmol) of 5-carbamoyl-4-(4-nitrophenyl)-1H-pyrrole-3-carboxylic acid. After hydrogenating for 3 hours in an autoclave under 3 bar of hydrogen, at a temperature in the region of 30° C., the reaction mixture is taken up in 5 cm³ of a 4N solution of hydrogen chloride in dioxane, and then filtered. The catalyst is rinsed with twice 2 cm³ of a 4N solution of hydrogen chloride in dioxane, and the filtrate is then concentrated to dryness under reduced pressure (2.7 kPa) to give 0.141 g of 5-carbamoyl-4-(4-aminophenyl)-1H-pyrrole-3-carboxylic acid hydrochloride in the form of a yellow solid; ES+: m/z=246: [M+H]+

5-Carbamoyl-4-(4-nitrophenyl)-1H-pyrrole-3-carboxylic acid may be Prepared as Described in Example 2

EXAMPLE 39

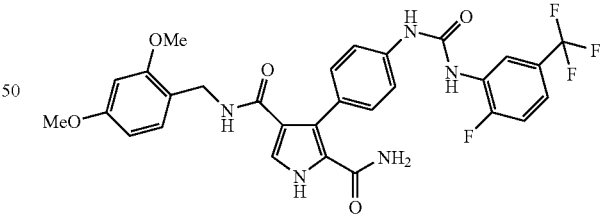

4-(2,4-Dimethoxybenzylamino)carbonyl-3-{4-[3-(2-fluoro-5-trifluoromethyl-phenyl)ureido]phenyl}-1H-pyrrole-2-carboxamide To 0.321 cm³ (2.09 mmol) of 2,4-dimethoxybenzylamine dissolved in 10 cm³ of toluene are added, at a temperature in the region of 20° C. under an argon atmosphere, 1.36 cm³ (2.717 mmol) of a 2M solution of trimethylaluminium in toluene, followed by addition of 0.5 g (1.045 mmol) of ethyl 5-carbamoyl-4-{4-[3-(2-fluoro-5-trifluoromethylphenyl)

ureido]phenyl}-1H-pyrrole-3-carboxylate. After stirring for 16 hours at a temperature in the region of 60° C., the reaction mixture is diluted with 50 cm³ of ethyl acetate and then washed successively with twice 30 cm³ of saturated ammonium chloride solution and twice 25 cm³ of water. The organic phase obtained is dried over anhydrous magnesium sulfate, filtered and concentrated to dryness under reduced pressure (2.7 kPa) to give 0.52 g of a yellow solid, which is purified by flash chromatography [eluent: dichloromethane/methanol/acetonitrile (90/5/5 by volume)]. After concentrating the fractions under reduced pressure, 0.170 g of 4-(2,4-dimethoxybenzylamino)carbonyl-3-{4-[3-(2-fluoro-5-trifluoromethyl-phenyl)ureido]phenyl}-1H-pyrrole-2-carboxamide is obtained in the form of a yellow solid melting at a temperature above 260° C.; ¹H NMR (400 MHz, DMSO d6, δ in ppm): 3.68 (s, 3H); 3.70 (s, 3H); 4.12 (d, J=6.0 Hz, 2H); 5.34 (broad m, 1H); 6.40 (dd, J=2.5 and 8.5 Hz, 1H); 6.46 (d, J=2.5 Hz, 1H); 6.86 (d, J=8.5 Hz, 1H); 6.99 (t, J=6.0 Hz, 1H); 7.17 (broad m, 1H); 7.23 (d, J=8.5 Hz, 2H); 7.39 (m, 1H); 7.43 (d, J=2.5 Hz, 1H); 7.50 (partially masked m, 1H); 7.51 (d, J=8.5 Hz, 2H); 8.64 (dd, J=2.5 and 7.5 Hz, 1H); 9.00 (broad s, 1H); 9.36 (broad s, 1H); 11.85 (broad s, 1H); ES⁺: m/z=600: [M+H]⁺.

Ethyl 5-carbamoyl-4-{4-[3-(2-fluoro-5-trifluoromethylphenyl)ureido]phenyl}-1H-pyrrole-3-carboxylate may be Prepared as Described in Example 9

EXAMPLE 40

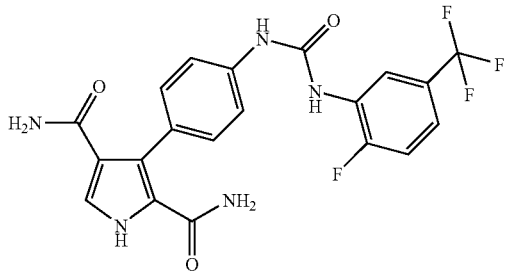

3-{4-[3-(2-Fluoro-5-trifluoromethylphenyl)ureido]phenyl}-1H-pyrrole-2,4-dicarboxamide To 0.15 g (0.25 mmol) of 4-(2,4-dimethoxybenzylamino)carbonyl-3-{4-[3-(2-fluoro-5-trifluoromethylphenyl)ureido]phenyl}-1H-pyrrole-2-carboxamide dissolved in 3 cm³ of toluene is added, at a temperature in the region of 20° C. under an argon atmosphere, 0.108 g of p-toluenesulfonic acid monohydrate. After stirring for 48 hours at a temperature in the region of 65° C., the reaction mixture is diluted with 0.25 cm³ of methanol and the pH is then adjusted to a value of between 12 and 13 by addition of aqueous 1N sodium hydroxide solution. The reaction medium is extracted with three times 15 cm³ of ethyl acetate. The organic phase is washed successively with 20 cm³ of water and 20 cm³ of saturated aqueous sodium chloride solution and then dried over anhydrous magnesium sulfate, filtered and concentrated to dryness under reduced pressure (2.7 kPa) to give 0.175 g of a yellow solid, which is purified by flash chromatography [eluent: dichloromethane/methanol/acetonitrile (90/5/5 by volume)]. After concentrating the fractions under reduced pressure, 0.047 g of 3-{4-[3-(2-fluoro-5-trifluoromethylphenyl)ureido]phenyl}-1H-pyrrole-2,4-dicarboxamide is obtained in the form of a white solid melting at 196° C.; ¹H NMR (400 MHz, DMSO d6, δ in ppm): 5.32 (broad m, 1H); 6.41 to 6.77 (broad m, 2H); 7.15 (broad m, 1H); 7.24 (d, J=8.5 Hz, 2H); 7.39 (m, 1H); 7.45 (broad s, 1H); 7.50 (partially masked m, 1H); 7.52 (d, J=8.5 Hz, 2H); 8.62 (dd, J=2.0 and 7.5 Hz, 1H); 9.11 (broad s, 1H); 9.46 (broad s, 1H); 11.85 (broad s,1H); ES⁺: m/z=450: [M+H]⁺.

4-(2,4-Dimethoxybenzylamino)carbonyl-3-{4-[3-(2-fluoro-5-trifluoromethyl-phenyl)ureido]phenyl}-1H-pyrrole-2-carboxamide may be Prepared as Described in Example 39

EXAMPLE 41

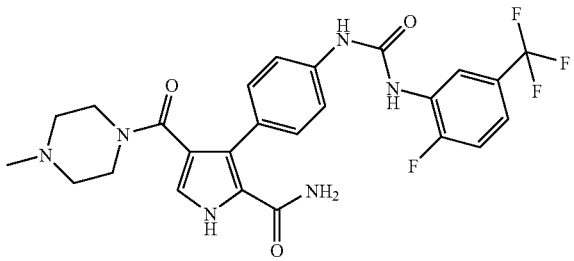

3-{4-[3-(2-Fluoro-5-trifluoromethylphenyl)ureido]phenyl}-4-(4-methylpiperazine-1-carbonyl)-1H-pyrrole-2-carboxamide The process is performed in a manner similar to that described in Example 39 but starting with N-methylpiperazine and ethyl 5-carbamoyl-4-{4-[3-(2-fluoro-5-trifluoromethylphenyl)ureido]phenyl}-1H-pyrrole-3-carboxylate. After a similar work-up, 3-{4-[3-(2-fluoro-5-trifluoromethylphenyl)ureido]phenyl}-4-(4-methylpiperazine-1-carbonyl)-1H-pyrrole-2-carboxamide is obtained; ES⁺: m/z=533 [M+H]⁺.

Ethyl 5-carbamoyl-4-{4-[3-(2-fluoro-5-trifluoromethylphenyl)ureido]phenyl}-1H-pyrrole-3-carboxylate may be Prepared as Described in Example 9

EXAMPLE 42

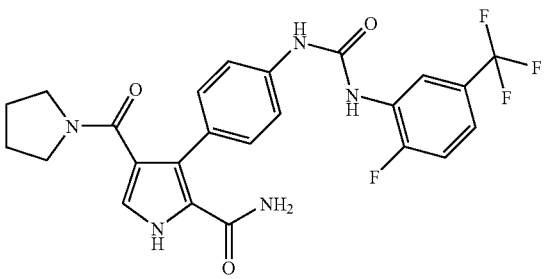

3-{4-[3-(2-Fluoro-5-trifluoromethylphenyl)ureido]phenyl}-4-(pyrrolidine-1-carbonyl)-1H-pyrrole-2-carboxamide The process is performed in a manner similar to that described in Example 39 but starting with pyrrolidine and ethyl 5-carbamoyl-4-{4-[3-(2-fluoro-5-trifluoromethylphenyl)ureido]phenyl}-1H-pyrrole-3-carboxylate. After a similar work-up, 3-{4-[3-(2-fluoro-5-trifluoromethylphenyl)ureido]phenyl}-4-(pyrrolidine-1-carbonyl)-1H-pyrrole-2-carboxamide is obtained; ES+: m/z=504 [M+H]+.

Ethyl 5-carbamoyl-4-{4-[3-(2-fluoro-5-trifluoromethylphenyl)ureido]phenyl}-1H-pyrrole-3-carboxylate may be Prepared as Described in Example 9

EXAMPLE 43

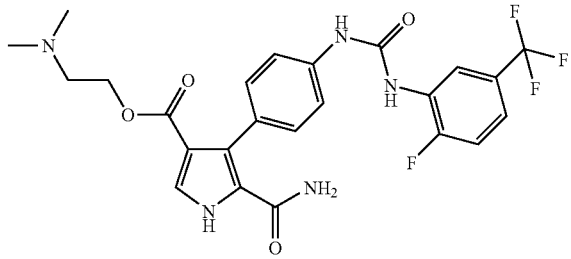

2-Dimethylaminoethyl 5-carbamoyl-4-{4-[3-(2-fluoro-5-trifluoromethylphenyl)-ureido]phenyl}-1H-pyrrole-3-carboxylate To 0.12 g (0.266 mmol) of ethyl 5-carbamoyl-4-{4-[3-(2-fluoro-5-trifluoromethylphenyl)ureido]phenyl}-1H-pyrrole-3-carboxylate dissolved in 4 cm³ of dimethylformamide are added, at a temperature in the region of 20° C. under an argon atmosphere, 0.06 cm³ of 2-dimethylaminoethanol, 0.085 cm³ of triethylamine, 112 mg 1-(3-dimethylaminopropyl)-3-ethylcarbodiimide hydrochloride and 80 mg of 1-hydroxybenzotriazole hydrate. After stirring for 3 hours at a temperature in the region of 70° C., the reaction mixture is poured into 40 cm³ of distilled water and then stirred for 1 hour at a temperature in the region of 20° C. The reaction mixture is filtered through a No. 3 sinter funnel and the solid is washed with twice 5 cm³ of water and then air-dried to give 0.065 g of a white solid, which is purified by flash chromatography [eluent: dichloromethane/methanol/28% aqueous ammonia (12/2.25/0.38 by volume)]. After concentrating the fractions under reduced pressure, 0.04 g of 2-dimethylaminoethyl 5-carbamoyl4-{4-[3-(2-fluoro-5-trifluoromethylphenyl)ureido]phenyl}-1H-pyrrole-3-carboxylate is obtained in the form of a white solid; ES+: m/z=522 [M+H]+.

Ethyl 5-carbamoyl-4-{4-[3-(2-fluoro-5-trifluoromethylphenyl)ureido]phenyl}-1H-pyrrole-3-carboxylate may be prepared as described in Example 9

EXAMPLE 44

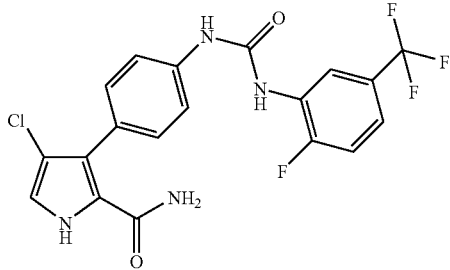

4-Chloro-3-{4-[3-(2-fluoro-5-trifluoromethylphenyl)ureido]phenyl}-1H-pyrrole-2-carboxamide To 0.03 g (0.127 mmol) of 4-chloro-3-(4-aminophenyl)-1H-pyrrole-2-carboxamide dissolved in 2.7 cm³ of tetrahydrofuran is added, at a temperature in the region of 20° C. under an argon atmosphere, 0.019 cm³ (0.134 mmol) of 2-fluoro-5-trifluoromethylphenyl isocyanate. After stirring for 2 hours at a temperature in the region of 20° C., the reaction mixture is concentrated to dryness under reduced pressure (2.7 kPa) to give a residue, which is recrystallized from 4 cm³ of acetonitrile. After filtering through a No. 3 sinter funnel, the solid is washed with 2 cm³ of acetonitrile and then dried under reduced pressure (2.7 kPa) at a temperature in the region of 45° C. for 2 hours to give 0.037 g of 4-chloro-3-{4-[3-(2-fluoro-5-trifluoromethylphenyl)-ureido]phenyl}-1H-pyrrole-2-carboxamide in the form of a white solid; ¹H NMR (400 MHz, DMSO d6, δ in ppm): 5.83 (broad m, 1H); 7.08 (s, 1H); 7.18 (broad m, 1H); 7.28 (d, J=8.5 Hz, 2H); 7.38 (m, 1H); 7.50 (partially masked m, 1H); 7.55 (d, J=8.5 Hz, 2H); 8.62 (dd, J=2.0 and 7.5 Hz, 1H); 9.04 (broad s, 1H); 9.39 (broad s, 1H); 11.8 (broad s, 1H); ES+: m/z=441: [M+H]+; ES−: m/z=439: [M−H]−.

4-Chloro-3-(4-aminophenyl)-1H-pyrrole-2-carboxamide may be prepared in the following manner To 0.136 g (0.512 mmol) of 4-chloro-3-(4-nitrophenyl)-1H-pyrrole-2-carboxamide dissolved in 2.8 cm³ of acetic acid are added, at a temperature in the region of 20° C. under an argon atmosphere, 134 mg (2.048 mmol) of zinc powder. After stirring for 2 hours at a temperature in the region of 20° C., the reaction mixture is diluted with 20 cm³ of ethyl acetate and 15 cm³ of water and the pH is then adjusted to value of between 8 and 9 by adding aqueous 1N sodium hydroxide solution. The aqueous phase is extracted with twice 15 cm³ of ethyl acetate. The combined organic phases are dried over anhydrous magnesium sulfate, filtered and concentrated to dryness under reduced pressure (2.7 kPa) to give 0.145 g of an orange solid, which is purified by flash chromatography [eluent: dichloromethane/methanol/acetonitrile (90/5/5 by volume)]. After concentrating the fractions under reduced pressure, 0.03 g of 4-chloro-3-(4-aminophenyl)-1H-pyrrole-2-carboxamide is obtained in the form of a beige-coloured solid; EI: m/z=235: M+; m/z=218 [M−NH₂]+; m/z=155 [M-Cl—CONH₃]+; m/z=44 [CONH₂]+ base peak.

4-Chloro-3-(4-nitrophenyl)-1H-pyrrole-2-carboxamide and 5-chloro-3-(4-nitrophenyl)-1H-pyrrole-2-carboxamide may be Obtained in the Following Manner To 0.495 g (2.141 mmol) of 3-(4-nitrophenyl)-1H-pyrrole-2-carboxamide dissolved in 13.7 cm³ of acetonitrile are added, at a temperature in the region of 20° C. under an argon atmosphere, 286 mg (1.868 mmol) of N-chloro-succinimide powder. After stirring for 16 hours at a temperature in the region of 65° C., the reaction mixture is diluted with 40 cm³ of ethyl acetate and then washed successively with three times 20 cm³ of water and 20 cm³ of saturated aqueous sodium chloride solution. The resulting organic phase is then dried over anhydrous magnesium sulfate, filtered and concentrated to dryness under reduced pressure (2.7 kPa) to give 0.45 g of a red solid, which is purified by flash chromatography [eluent: dichloromethane/methanol/acetonitrile 98/1/1 by volume)]. After concentrating the fractions under reduced pressure, 0.3 g of a mixture of 4-chloro-3-(4-nitrophenyl)-1H-pyrrole-2-carboxamide and 5-chloro-3-(4-nitrophenyl)-1H-pyrrole-2-carboxamide, in respective proportions of 55/45, is obtained in the form of an orange-coloured solid, which is purified by preparative LC-MS HPLC:

| Technique | Detection | Mobile phase A | Mobile phase B |
|---|---|---|---|
| Preparative LC-MS | Diode array | H₂O + 0.1% TFA pH = 1 | acetonitrile |

| Gradient | | |
|---|---|---|
| Time min | Flow rate ml/min | % acetonitrile |
| 0 | 20 | 25 |
| 1 | 20 | 25 |
| 3 | 30 | 25 |
| 11 | 30 | 40 |
| 12 | 30 | 100 |
| 12.80 | 20 | 100 |

The two isomers are separated by chromatography:

| Technique | Detection | Stationary phase | Mobile phase | Flow rate |
|---|---|---|---|---|
| Prochrom 2 Axxial column | UV 254 nm | WHELK01.SS MIXT.700 G 350 × 80 mm, 10 μm | 70% Heptane; 28% CH₂Cl₂; 2% MeOH; 0.1% TEA | 92 ml/min |

Chemical purity:

| Technique | Detection | Stationary phase | Mobile phase | Flow rate |
|---|---|---|---|---|
| Platform | TIC | Thermo hypersil gold 50 × 3 mm, 3 μm | Gradient 7 min A: H₂O + 0.1% HCOOH B: acetonitrile | 0.8 ml/min |

Analytical controls, reverse-phase HPLC purity:

| Technique | Detection | Stationary phase | Mobile phase | Flow rate |
|---|---|---|---|---|
| Agilent 1 | UV 265 nm | Whelk01.SS 10 μm 250 × 4.6 mm | 70% Heptane; 28% CH₂Cl₂; 2% MeOH; 0.1% TEA | 1 ml/min |

| | Isomer 5-Cl | Isomer 4-Cl |
|---|---|---|
| Retention time | 16.23 min | 18.59 min |
| Purity | >99% | 98% |

Thus, 0.136 g of 4-chloro-3-(4-nitrophenyl)-1H-pyrrole-2-carboxamide is obtained in the form of a yellow solid; EI: m/z=265: M⁺ base peak; m/z=248 [M−NH₃]⁺; m/z=218 [248−NO]⁺.

and 0.120 mg of 5-chloro-3-(4-nitrophenyl)-1H-pyrrole-2-carboxamide is obtained in the form of a yellow solid; EI: m/z=265: M⁺ base peak; m/z=248 [M−NH₃]⁺; m/z=218 [248−NO]⁺.

3-(4-Nitrophenyl)-1H-pyrrole-2-carboxamide may be Prepared in the Following Manner To 1.96 g (5.139 mmol) of 2-(2,4-dimethoxybenzylamino)carbonyl-3-(4-nitrophenyl)-1H-pyrrole dissolved in 55 cm³ of toluene are added, at a temperature in the region of 20° C. under an argon atmosphere, 2.224 g (11.69 mmol) p-toluenesulfonic acid monohydrate. After stirring for 4.5 hours at a temperature in the region of 65° C., the reaction mixture is diluted with 70 cm³ of ethyl acetate and then washed successively with three times 50 cm³ of water and 50 cm³ of saturated aqueous sodium chloride solution. The resulting organic phase is dried over anhydrous magnesium sulfate, filtered and concentrated to dryness under reduced pressure (2.7 kPa) to give a yellow solid, which is then stirred in 15 cm³ of acetonitrile for 16 hours. After filtering through a No. 3 sinter funnel, the solid is washed with twice 4 cm³ of ice-cold acetonitrile and then dried under reduced pressure (2.7 kPa) at a temperature in the region of 35° C. for 5 hours to give 0.5 g of 3-(4-nitrophenyl)-1H-pyrrole-2-carboxamide in the form of an ochre-coloured solid; EI: m/z=231: M⁺ base peak; m/z=214 [M−NH₃]⁺; m/z=184 [M−HNO₂]⁺.

2-(2,4-Dimethoxybenzylamino)carbonyl-3-(4-nitrophenyl)-1H-pyrrole may be Prepared in the Following Manner To 2.435 cm³ (15.84 mmol) of 2,4-dimethoxybenzylamine dissolved in 65 cm³ of toluene are added, at a temperature in the region of 20° C. under an argon atmosphere, 10.3 cm³ (20.59 mmol) of a 2M solution of trimethylaluminium in toluene, followed by addition of 1.95 g (7.92 mmol) of methyl 3-(4-nitrophenyl)-1H-pyrrole-2-carboxylate. After stirring for 1 hour at a temperature in the region of 20° C. and then for 16 hours at a temperature in the region of 60° C., the reaction mixture is diluted with 170 cm³ of ethyl acetate. The resulting solution is washed successively with three times 70 cm³ of saturated aqueous ammonium chloride solution and twice 50 cm³ of water and then dried over anhydrous magnesium sulfate, filtered and concentrated to dryness under reduced pressure (2.7 kPa) to give a yellow solid, which is then stirred in 20 cm³ of acetonitrile at a temperature in the region of 5° C. for 30 minutes. After filtering through a No. 3 sinter funnel, the solid is washed with 10 cm³ of ice-cold acetonitrile and then dried under reduced pressure (2.7 kPa) at a temperature in the region of 35° C. for 3 hours to give 1.96 g of 2-(2,4-dimethoxybenzylamino)carbonyl-3-(4-nitrophenyl)-1H-pyrrole in the form of a yellow solid; ES⁺: m/z=382: [M+H]⁺; ES⁻: m/z=380: [M−H]⁻.

Methyl 3-(4-nitrophenyl)-1H-pyrrole-2-carboxylate may be prepared as described in Example 1

EXAMPLE 45

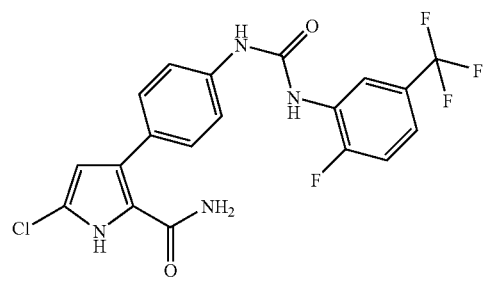

5-Chloro-3-{4-[3-(2-fluoro-5-trifluoromethylphenyl) ureido]phenyl}-1H-pyrrole-2-carboxamide To 0.055 g (0.233 mmol) of 5-chloro-3-(4-aminophenyl)-1H-pyrrole-2-carboxamide dissolved in 5 cm³ of tetrahydrofuran is added, at a temperature in the region of 20° C. under an argon atmosphere, 0.035 cm³ (0.245 mmol) of 2-fluoro-5-trifluoromethylphenyl isocyanate. After stirring for 2 hours at a temperature in the region of 20° C., the reaction mixture is concentrated to dryness under reduced pressure (2.7 kPa) to give a residue, which is recrystallized from 4 cm³ of acetonitrile. After filtering through a No. 3 sinter funnel, the solid is washed with 2 cm³ of acetonitrile and then dried under reduced pressure (2.7 kPa) at a temperature in the region of 35° C. for 4 hours to give 0.076 g of 5-chloro-3-{4-[3-(2-fluoro-5-trifluoromethylphenyl)ureido]-phenyl}-1H-pyrrole-2-carboxamide in the form of a yellow solid; $^1$H NMR (400 MHz, DMSO d6, δ in ppm): 6.16 (s, 1H); 6.45 (broad m, 1H); 7.12 (broad m, 1H); 7.38 (partially masked m, 1H); 7.40 (d, J=9.0 Hz, 2H); 7.45 (d, J=9.0 Hz, 2H); 7.49 (dd, J=9.0 and 11.0 Hz, 1H); 8.63 (dd, J=2.0 and 7.5 Hz, 1H); 8.90 (d, J=2.5 Hz, 1H); 9.22 (s, 1H); 12.1 (broad m, 1H); ES$^+$: m/z=291: [M+Na]$^+$.

5-Chloro-3-(4-aminophenyl)-1H-pyrrole-2-carboxamide may be prepared in the following manner To 0.12 g (0.452 mmol) of 5-chloro-3-(4-nitrophenyl)-1H-pyrrole-2-carboxamide dissolved in 2.36 cm³ of acetic acid are added, at a temperature in the region of 20° C. under an argon atmosphere, 118 mg (1.806 mmol) of zinc powder. After stirring for 2 hours at a temperature in the region of 20° C., the reaction mixture is diluted with 30 cm³ of ethyl acetate and 15 cm³ of water, and the pH is then adjusted to a value of between 8 and 9 by addition of aqueous 1N sodium hydroxide solution. The aqueous phase is extracted with twice 20 cm³ of ethyl acetate. The organic phases are combined, dried over anhydrous magnesium sulfate, filtered and concentrated to dryness under reduced pressure (2.7 kPa) to give 0.103 g of an orange solid, which is purified by flash chromatography [eluent: dichloromethane/methanol/acetonitrile (90/5/5 by volume)]. After concentrating the fractions under reduced pressure, 0.055 g of 5-chloro-3-(4-aminophenyl)-1H-pyrrole-2-carboxamide is obtained in the form of a yellow solid; EI: m/z=235: M$^+$; m/z=218 [M–NH$_2$]$^+$; m/z=155 [M–Cl—CONH$_3$]$^+$; m/z=44 [CONH$_2$]$^+$ base peak.

Methyl 3-(4-nitrophenyl)-1H-pyrrole-2-carboxylate may be prepared as described in Example 44

EXAMPLE 46

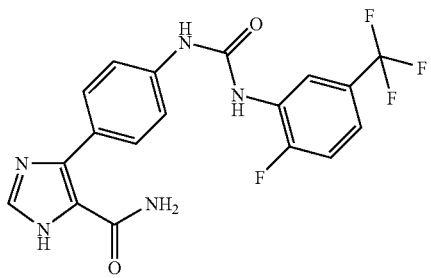

5-{4-[3-(2-Fluoro-5-trifluoromethylphenyl)ureido] phenyl}-3H-imidazole-4-carboxamide To 0.055 g (0.272 mmol) of 5-(4-aminophenyl)-3H-imidazole-4-carboxamide dissolved in 4 cm³ of tetrahydrofuran is added, at a temperature in the region of 20° C. under an argon atmosphere, 0.040 cm³ (0.272 mmol) of 2-fluoro-5-trifluoromethylphenyl isocyanate. After stirring for 16 hours at a temperature in the region of 20° C., the reaction mixture is filtered through a No. 3 sinter funnel. The solid obtained is washed successively with three times 2 cm³ of tetrahydrofuran and three times 2 cm³ of pentane and is then dried under reduced pressure (2.7 kPa) to give 0.058 g of 5-{4-[3-(2-fluoro-5-trifluoromethylphenyl)ureido]phenyl}-3H-imidazole-4-carboxamide in the form of a beige-coloured solid melting at 325° C.; $^1$H NMR (400 MHz, DMSO d6, δ in ppm) 6.98 (broad m, 1H); 7.30 (broad m, 1H); 7.40 (m, 1H); 7.49 (partially masked m, 1H); 7.51 (d, J=8.5 Hz, 2H); 7.71 (s, 1H); 7.82 (d, J=8.5 Hz, 2H); 8.62 (dd, J=2.0 and 7.5 Hz, 1H); 9.00 (broad s, 1H); 9.37 (broad s, 1H); 12.65 (broad m, 1H); EI: m/z=407: M$^+$; m/z=205 [C$_8$H$_3$NOF$_4$]$^+$ base peak; m/z=179 [C$_7$H$_5$NF$_4$]$^+$.

5-(4-Aminophenyl)-3H-imidazole-4-carboxamide may be Prepared in the Following Manner To a suspension of 0.009 g (0.081 mmol) of 10% palladium-on-charcoal in 20 cm³ of methanol is added, at a temperature in the region of 20° C., 0.04 g (0.172 mmol) of 5-(4-nitrophenyl)-3H-imidazole-4-carboxamide. After hydrogenating for 3 hours in an autoclave under 3 bar of hydrogen, at a temperature in the region of 25° C., the reaction mixture is filtered. The catalyst is rinsed with twice 2 cm³ of methanol and the filtrate is then concentrated to dryness under reduced pressure (2.7 kPa) to give 0.034 g of 5-(4-aminophenyl)-3H-imidazole-4-carboxamide in the form of a brown solid; EI: m/z=202: M$^+$; CI: m/z=203: [M+H]$^+$; ES$^+$: m/z=203: [M+H]$^+$; ES$^-$: m/z=201: [M–H]$^-$.

5-(4-Nitrophenyl)-3H-imidazole-4-carboxamide may be Prepared in the Following Manner A solution of 0.05 g (0.192 mmol) of ethyl 5-(4-nitrophenyl)-3H-imidazole-4-carboxylate in 4 cm³ of a 7N solution of ammonia in methanol and 8 cm³ of aqueous 28% ammonia solution is heated in an autoclave at a temperature in the region of 80° C., under 12 bar, for 20 hours. After stopping the heating and returning to room temperature and pressure, the reaction mixture is concentrated to dryness under reduced pressure (2.7 kPa) to give 0.068 g of a solid, which is purified by flash chromatography [eluent: ethyl acetate/methanol (95/5 by volume)]. After concentrating the fractions under reduced pressure, 0.012 g of 5-(4-nitrophenyl)-3H-imidazole-4-carboxamide is obtained in the form of a white solid; EI: m/z=232: M$^+$; m/z=231 [M–H]$^-$ base peak; CI: m/z=233: [M+H]$^+$; m/z=250 [M+NH$_4$]$^+$ base peak.

Ethyl 5-(4-nitrophenyl)-3H-imidazole-4-carboxylate may be Prepared in the Following Manner To 4.572 g (59.32 mmol) of ammonium acetate dissolved in 60 cm³ of acetic acid are added, at a temperature in the region of 20° C. under an argon atmosphere, 1.493 g (5.93 mmol) of ethyl 3-(4-nitrophenyl)-2,3-dioxopropionate and 32.06 g (356 mmol) of formaldehyde. After stirring for 4 hours at a temperature in the region of 65° C., the reaction mixture is filtered through a No 3. sinter funnel. The solid obtained is washed with 50 cm³ of methanol and the filtrate is then concentrated to dryness under reduced pressure (2.7 kPa) to give a residue, which is taken up in 30 cm³ of dichloromethane. The resulting solution is washed successively with 30 cm³ of saturated aqueous sodium carbonate solution, 30 cm³ of water and 30 cm³ of saturated aqueous sodium chloride solution and then dried over anhydrous magnesium sulfate, filtered and concentrated to dryness under reduced pressure (2.7 kPa) to give a yellow solid, which is purified by flash chromatography [eluent: ethyl acetate/cyclohexane (4/1 by volume)]. After concentrating the fractions under reduced pressure, 0.197 g of ethyl 5-(4-nitrophenyl)-3H-imidazole-4-carboxylate is obtained in the form of a yellow solid; EI: m/z=261: M⁺ base peak; m/z=215 [M-HOEt]⁺.

Ethyl 3-(4-nitrophenyl)-2,3-dioxopropionate may be prepared as described in the literature by Dayer, Francis; Huu Le Dao; Gold, Hellmut; Rode-Gowal, Heike; Dahn, Hans; Helvetica Chimica Acta (1974), 57(7), 2201-9.

Determination of the Activity of the Compounds—Experimental Protocols

1. FAK

The inhibitory activity of the compounds on FAK is determined by measuring the inhibition of autophosphorylation of the enzyme using a time-resolved fluorescence test (HTRF).

The whole cDNA of human FAK, the N-terminal end of which has been labelled with histidine, was cloned in a pFastBac HTc baculovirus expression vector. The protein was expressed and purified to about 70% homogeneity.

The kinase activity is determined by incubating the enzyme (6.6 μg/mL) with different concentrations of test compound in a 50 mM Hepes pH=7.2, 10 mM MgCl$_2$, 100 μm Na$_3$VO$_4$, 15 μM ATP buffer for 1 hour at 37° C. The enzymatic reaction is stopped by adding Hepes pH=7.0 buffer containing 0.4 mM KF, 133 mM EDTA, 0.1% BSA and the labelling is performed, for 1 to 2 hours at room temperature, by adding to this buffer an anti-Histidine antibody labelled with XL665 and a tyrosine phosphospecific monoclonal antibody conjugated to europium cryptate (Eu-K). The characteristics of the two fluorophores are available in G. Mathis et al., Anticancer Research, 1997, 17, pages 3011-3014. The energy transfer from the excited europium cryptate to the acceptor XL665 is proportional to the degree of autophosphorylation of FAK. The long-lasting signal specific for XL-665 is measured in a Packard Discovery plate counter. All the tests are performed in duplicate and the average of the two tests is calculated. The inhibition of the autophosphorylation activity of FAK with compounds of the invention is expressed as a percentage of inhibition relative to a control whose activity is measured in the absence of test compound. To calculate the percentage inhibition, the ratio [signal at 665 nm/signal at 620 nm] is considered.

2. KDR

The inhibitory effect of the compounds is determined in an in vitro test of phosphorylation of substrate with the enzyme KDR via a scintillation technique (96-well plate, NEN).

The cytoplasmic domain of the human KDR enzyme was cloned in the form of a GST fusion in the pFastBac baculovirus expression vector. The protein was expressed in the SF21 cells and purified to about 60% homogeneity.

The KDR kinase activity is measured in 20 mM MOPS, 10 mM MgCl2, 10 mM MnCl$_2$, 1 mM DTT, 2.5 mM EGTA, 10 mM b-glycerophosphate, pH=7.2, in the presence of 10 mM MgCl$_2$, 100 μm Na$_3$VO$_4$, 1 mM NaF. 10 μl of the compound are added to 70 μL of kinase buffer containing 100 ng of KDR enzyme at 4° C. The reaction is initiated by adding 20 μL of solution containing 2 μg of substrate (SH2-SH3 fragment of PLCγ expressed in the form of a GST fusion protein), 2 μCi of γ$^{33}$P[ATP] and 2 μm of cold ATP. After incubation for 1 hour at 37° C., the reaction is stopped by adding 1 volume (100 μl) of 200 mM EDTA. The incubation buffer is removed, and the wells are washed three times with 300 μL of PBS. The radioactivity in each well is measured using a Top Count NXT radioactivity counter (Packard).

The background is determined by measuring the radioactivity in four different wells containing radioactive ATP and the substrate alone.

A total activity control is measured in four different wells containing all the reagents (γ$^{33}$P-[ATP], KDR and substrate PLCγ), but in the absence of compound.

The inhibition of the KDR activity with the compound of the invention is expressed as a percentage of inhibition of the control activity determined in the absence of compound.

Compound SU5614 (Calbiochem) (1 μm) is included in each plate as an inhibition control.

3. Tie2

The coding sequence of human Tie2 corresponding to the amino acids of the intracellular domain 776-1124 was generated by PCR using the cDNA isolated from a human placenta as a model. This sequence was introduced into a pFastBacGT baculovirus expression vector in the form of a GST fusion protein.

The inhibitory effect of the molecules is determined in a test of phosphorylation of PLC with Tie2 in the presence of GST-Tie2 purified to about 80% homogeneity. The substrate is composed of the SH2-SH3 fragments of PLC expressed in the form of a GST fusion protein.

The kinase activity of Tie2 is measured in a MOPS 20 mM pH 7.2 buffer, containing 10 mM MgCl$_2$, 10 mM MnCl$_2$, 1 mM DTT, 10 mM of glycerophosphate. In a 96-well FlashPlate plate maintained on ice, a reaction mixture is deposited, composed of 70 μL of kinase buffer containing 100 ng of enzyme GST-Tie2 per well. Next, 10 μL of the test molecule diluted in DMSO to a maximum concentration of 10% are added. For a given concentration, each measurement is performed four times. The reaction is initiated by adding 20 μL of solution containing 2 μg of GST-PLC, 2 μm of cold ATP and 1 μCi of $^{33}$P[ATP]. After incubation for one hour at 37° C., the reaction is stopped by adding 1 volume (100 μl) of EDTA 200 mM. After removal of the incubation buffer, the wells are washed three times with 300 μL of PBS. The radioactivity is measured on a MicroBeta1450 Wallac.

The inhibition of the Tie2 activity is calculated and expressed as a percentage of inhibition relative to the control activity determined in the absence of compound.

TABLE 1

Results:

| Structure | Example | FAK IC 50 (nM) | KDR IC 50 (nM) | TIE2 IC 50 (nM) |
|---|---|---|---|---|
| 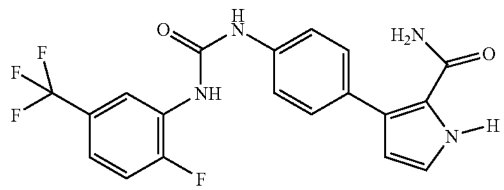 | 1 | 2381 | 115 | 13 |
| 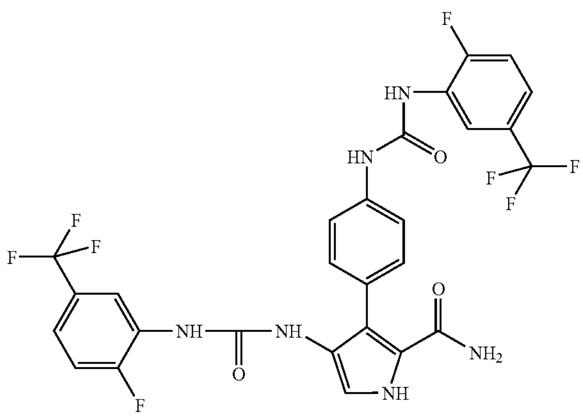 | 4 | — | 352 | 111 |
| 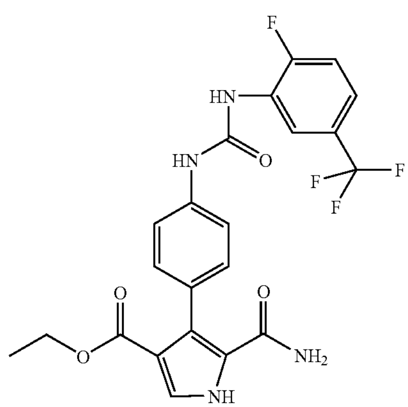 | 9 | — | 23 | 4 |
| 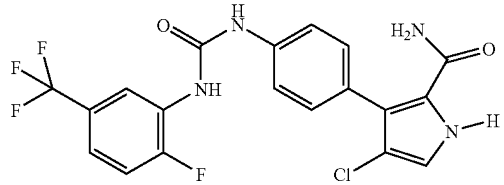 | 44 | — | 27 | 7 |

What is claimed is:

1. A compound of formula (I):

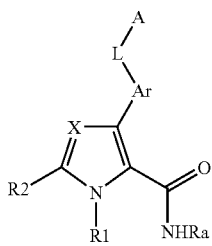

Formula (I)

in which:
1) A and Ar are independently selected from the group consisting of substituted and unsubstituted phenyl;
2) L is NH—CO—NH;
3) Ra is selected from the group consisting of H, alkyl and cycloalkyl;
4) R1 is selected from the group consisting of: H, R, COR, and SO₂R, in which R is chosen from H, OR"₄, NR"₅R"₆, (C1-C6)alkyl, cycloalkyl, heterocyclyl, substituted heterocyclyl, aryl, substituted aryl, heteroaryl and substituted heteroaryl, in which R"4 is chosen from H, phenyl and alkyl, and in which R"5 and R"6 are independently selected from the group consisting of H, OR"₄, (C1-C6)alkyl, cycloalkyl, heterocyclyl, substituted heterocyclyl, aryl, substituted aryl, heteroaryl and substituted heteroaryl, or alternatively R"5 and R"6 are linked together to form a saturated 5- to 8-membered ring containing from 0 to 3 hetero atoms chosen from O, S and N;
5) X is chosen from CR3 and N;
6) R2 and R3 are independently selected from the group consisting of: H, halogen, R'2, CN, O(R'2), OC(O)(R'2), OC(O)N(R'2)(R'3), OS(O₂)(R'2), N(R'2)(R'3), N=C (R'2)(R'3), N(R'2)C(O)(R'3), N(R'2)C(O)O(R'3), N(R'4)C(O)N(R'2)(R'3), N(R'4)C(S)N(R'2)(R'3), N(R'2)S(O₂)(R'3), C(O)(R'2), C(O)O(R'2), C(O)N(R'2)(R'3), C(=N(R'3))(R'2), C(=N(OR'3))(R'2), S(R'2), S(O)(R'2), S(O₂)(R'2), S(O₂)O(R'2), and S(O₂)N(R'2)(R'3); in which each R'2, R'3, and R'4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl and substituted heterocyclyl; in which, when R'2 and R'3 are each other than H and simultaneously present on R2 or on R3, they may be linked together to form a ring containing from 0 to 3 hetero atoms chosen from O, S and N; or
a pharmaceutically acceptable salt thereof wherein the compound may be in achiral form, or in racemic form or enriched in one stereoisomer or enriched in one enantiomer.

2. A compound according to claim 1, wherein Ar-L-A is:

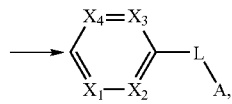

in which each X1, X2, X3 and X4 is independently C—R'5, in which R'5 has the same definition as R2 as defined in claim 1.

3. A compound according to claim 2, wherein R'5 is selected from the group consisting of H, F, Cl, methyl, NH₂, OMe; OCF₃ and CONH₂.

4. A compound according to claim 1, wherein R2 is a hydrogen atom.

5. A compound according to claim 1, wherein X is CR3.

6. A compound according to claim 1, wherein at least one from among R2 and R3 is a halogen.

7. A compound according to claim 1, wherein R3 is selected from the group consisting of H, halogen, NH₂, N(R'2)C(O)(R'3), N(R'2)C(O)O(R'3), N(R'4)C(O)N(R'2)(R'3), C(O)O(R'2) and C(O)N(R'2)(R'3); in which each R'2, R'3 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl and substituted heterocyclyl; in which, when R'2 and R'3 are each other than H and simultaneously present on R2 or on R3, they may be linked together to form a ring containing from 0 to 3 hetero atoms chosen from O, S and N.

8. A compound according to claim 7, wherein R3 is selected from the group consisting of H, halogen, NH₂, NH—COO-alkyl and —NH—CO—NH-aryl in which the aryl is unsubstituted or substituted with one or more halogen or haloalkyl, —NH—CO-alkyl, —NH—CO-alkyl-N(alkyl)(alkyl'), —COOH, —COO-alkyl, —COO-alkyl-N(alkyl)(alkyl') or —CO—NH-alkyl-aryl in which the aryl is unsubstituted or substituted with one or more alkoxy, —CONH₂— or —CO-heterocyclyl in which the heterocyclyl is unsubstituted or substituted with one or more alkyls.

9. A compound according to claim 1, wherein R1 is H.

10. A compound according to claim 1, wherein Ra is H.

11. A compound according to claim 1, wherein A is substituted with a first substituent selected from the group consisting of alkyl, haloalkyl, alkylene, alkynyl, aryl, heteroaryl, O-alkyl, O-Aryl, O-heteroaryl, S-alkyl, substituted S-alkyl, S-Aryl and S-heteroaryl, each being optionally substituted with a substituent chosen from (C1-C3)alkyl, halogen and O—(C1-C3)alkyl.

12. A compound according to claim 1, wherein A is substituted with a second substituent chosen from the group consisting of F, Cl, Br, I, OH, SH, SO₃M, COOM, CN, NO₂, CON(R8)(R9), N(R8)CO(R9), (C1-C3)alkyl-OH, (C1-C3) alkyl-N(R8)(R9), (C1-C3)alkyl-(R10), (C1-C3)alkyl-COOH and N(R8)(R9); in which R8 and R9 are independently chosen from H, (C1-C3)alkyl, (C1-C3)haloalkyl, (C1-C3)alkylOH, (C1-C3)alkylNH₂, (C1-C3)alkylCOOM and (C1-C3) alkylSO₃M; in which, when R8 and R9 are simultaneously other than H, they may be linked together to form a 5- to 7-membered ring containing from 0 to 3 hetero atoms chosen from N, O and S; in which M is H or a cation of an alkali metal chosen from Li, Na and K; and in which R10 is H or an optionally substituted non-aromatic heterocycle containing from 2 to 7 carbon atoms and 1 to 3 hetero atoms chosen from N, O and S.

13. A compound according to claim 11, wherein A is substituted with a second substituent chosen from the group consisting of F, Cl, Br, I, OH, SH, SO₃M, COOM, CN, NO₂, CON(R8)(R9), N(R8)CO(R9), (C1-C3)alkyl-OH, (C1-C3) alkyl-N(R8)(R9), (C1-C3)alkyl-(R10), (C1-C3)alkyl-COOH and N(R8)(R9); in which R8 and R9 are independently chosen from H, (C1-C3)alkyl, (C1-C3)haloalkyl, (C1-C3)alkylOH, (C1-C3)alkylNH₂, (C1-C3)alkylCOOM and (C1-C3) alkylSO₃M; in which, when R8 and R9 are simultaneously other than H, they may be linked together to form a 5- to 7-membered ring containing from 0 to 3 hetero atoms chosen from N, O and S; in which M is H or a cation of an alkali metal chosen from Li, Na and K; and in which R10 is H or an optionally substituted non-aromatic heterocycle containing from 2 to 7 carbon atoms and 1 to 3 hetero atoms chosen from N, O and S.

14. A compound according to claim 1, wherein A is phenyl substituted with one or more substituents selected from halogen, (C1-C4)alkyl, (C1-C3)haloalkyl, O—(C1-C4)alkyl, S—(C1-C4)alkyl, O—(C1-C4)haloalkyl and S—(C1-C4)haloalkyl, and when A is disubstituted, the two substituents may be linked together to form a 5- to 7-membered ring containing from 0 to 3 hetero atoms chosen from O, N and S.

15. A compound according to claim 1, wherein A is substituted with one or more substituents, which may be identical or different, independently selected from the group consisting of F, Cl, Br, I, OH, SH, $SO_3M$, COOM, CN, $NO_2$, CON(R8)(R9), N(R8)CO(R9), (C1-C3)alkyl-OH, (C1-C3)alkyl-N(R8)(R9), (C1-C3)alkyl-(R10), (C1-C3)alkyl-COOH, N(R8)(R9), (C1-C6)alkyl, (C2-C6)alkylene, (C2-C6)alkynyl, aryl, heteroaryl, O—(C1-C6)alkyl, O-Aryl, O-heteroaryl, S—(C1-C6)alkyl, S-Aryl and S—heteroaryl, each being optionally substituted with one or more substituents chosen from (C1-C3)alkyl, halogen and O—(C1-C3)alkyl; in which R8 and R9 are independently chosen from H, (C1-C3)alkyl, (C1-C3)alkylOH, (C1-C3)alkyl$NH_2$, (C1-C3)alkylCOOM and (C1-C3)alkyl$SO_3M$; in which, when R8 and R9 are simultaneously other than H, they may be linked together to form a 5- to 7-membered ring containing from 0 to 3 hetero atoms chosen from O, N and S; in which M is H or a cation of an alkali metal chosen from Li, Na and K; and in which R10 is H or an optionally substituted non-aromatic heterocycle, containing 2 to 7 carbon atoms and 1 to 3 hetero atoms chosen from N, O and S.

16. A compound according to claim 1, selected from the group consisting of:

3-{4-[3-(2-Fluoro-5-trifluoromethylphenyl)ureido]phenyl}-1H-pyrrole-2-carboxamide;

4-tert-Butyloxycarbonylamino-3-{4-[3-(2-fluoro-5-trifluoromethylphenyl)ureido]phenyl}-1H-pyrrole-2-carboxamide;

4-Amino-3-{4-[3-(2-fluoro-5-trifluoromethylphenyl)ureido]phenyl}-1H-pyrrole-2-carboxamide hydrochloride;

4-[3-(2-Fluoro-5-trifluoromethylphenyl)ureido]-3-{4-[3-(2-fluoro-5-trifluoromethyl-phenyl)ureido]phenyl}-1H-pyrrole-2-carboxamide;

4-Acetylamino-3-{4-[3-(2-fluoro-5-trifluoromethylphenyl)ureido]phenyl}-1H-pyrrole-2-carboxamide;

4-(2-Dimethylaminoacetylamino)-3-{4-[3-(2-fluoro-5-trifluoromethylphenyl)ureido]phenyl}-1H-pyrrole-2-carboxamide;

4-Benzoylamino-3-{4-[3-(2-fluoro-5-trifluoromethylphenyl)ureido]phenyl}-1H-pyrrole-2-carboxamide;

4-Nicotinoylamino-3-{4-[3-(2-fluoro-5-trifluoromethylphenyl)ureido]phenyl}-1H-pyrrole-2-carboxamide;

Ethyl 5-carbamoyl-4-{4-[3-(2-fluoro-5-trifluoromethylphenyl)ureido]phenyl}-1H-pyrrole-3-carboxylate;

Ethyl 5-carbamoyl-4-{4-[3-(2-fluorophenyl)ureido]phenyl}-1H-pyrrole-3-carboxylate;

Ethyl 5-carbamoyl-4-{4-[3-(2-methoxyphenyl)ureido]phenyl}-1H-pyrrole-3-carboxylate;

Ethyl 5-carbamoyl-4-{4-[3-(2-trifluoromethylphenyl)ureido]phenyl}-1H-pyrrole-3-carboxylate;

Ethyl 5-carbamoyl-4-[4-(3-o-tolylureido)phenyl]-1H-pyrrole-3-carboxylate;

Ethyl 5-carbamoyl-4-{4-[3-(3-fluorophenyl)ureido]phenyl}-1H-pyrrole-3-carboxylate;

Ethyl 5-carbamoyl-4-{4-[3-(3-methoxyphenyl)ureido]phenyl}-1H-pyrrole-3-carboxylate;

Ethyl 5-carbamoyl-4-{4-[3-(3-trifluoromethylphenyl)ureido]phenyl}-1H-pyrrole-3-carboxylate;

Ethyl 5-carbamoyl-4-[4-(3-m-tolylureido)phenyl]-1H-pyrrole-3-carboxylate;

Ethyl 5-carbamoyl-4-{4-[3-(4-fluorophenyl)ureido]phenyl}-1H-pyrrole-3-carboxylate;

Ethyl 5-carbamoyl-4-{4-[3-(4-methoxyphenyl)ureido]phenyl}-1H-pyrrole-3-carboxylate;

Ethyl 5-carbamoyl-4-{4-[3-(4-trifluoromethylphenyl)ureido]phenyl}-1H-pyrrole-3-carboxylate;

Ethyl 5-carbamoyl-4-[4-(3-p-tolylureido)phenyl]-1H-pyrrole-3-carboxylate;

Ethyl 5-carbamoyl-4-{4-[3-(4-chloro-3-trifluoromethylphenyl)ureido]phenyl}-1H-pyrrole-3-carboxylate;

Ethyl 5-carbamoyl-4-{4-[3-(2-chloro-5-trifluoromethylphenyl)ureido]phenyl}-1H-pyrrole-3-carboxylate;

Ethyl 5-carbamoyl-4-{4-[3-(2-fluoro-3-trifluoromethylphenyl)ureido]phenyl}-1H-pyrrole-3-carboxylate;

Ethyl 5-carbamoyl-4-{4-[3-(4-fluoro-3-trifluoromethylphenyl)ureido]phenyl}-1H-pyrrole-3-carboxylate;

Ethyl 5-carbamoyl-4-{4-[3-(3-fluoro-5-trifluoromethylphenyl)ureido]phenyl}-1H-pyrrole-3-carboxylate;

Ethyl 5-carbamoyl-4-{4-[3-(4-methyl-3-trifluoromethylphenyl)ureido]phenyl}-1H-pyrrole-3-carboxylate;

Ethyl 5-carbamoyl-4-{4-[3-(4-trifluoromethoxyphenyl)ureido]phenyl}-1H-pyrrole-3-carboxylate;

Ethyl 5-carbamoyl-4-{4-[3-(4-difluoromethoxyphenyl)ureido]phenyl}-1H-pyrrole-3-carboxylate;

Ethyl 5-carbamoyl-4-{4-[3-(3,4-dimethylphenyl)ureido]phenyl}-1H-pyrrole-3-carboxylate;

Ethyl 5-carbamoyl-4-{4-[3-(3,4-dimethoxyphenyl)ureido]phenyl}-1H-pyrrole-3-carboxylate;

Ethyl 5-carbamoyl-4-{4-[3-(3,5-dimethoxyphenyl)ureido]phenyl}-1H-pyrrole-3-carboxylate;

Ethyl 5-carbamoyl-4-{4-[3-(2,5-dimethylphenyl)ureido]phenyl}-1H-pyrrole-3-carboxylate;

Ethyl 5-carbamoyl-4-{4-[3-(2-methoxy-5-methylphenyl)ureido]phenyl}-1H-pyrrole-3-carboxylate;

Ethyl 5-carbamoyl-4-{4-[3-(2,5-dimethoxyphenyl)ureido]phenyl}-1H-pyrrole-3-carboxylate;

Ethyl 5-carbamoyl-4-{4-[3-(3-chloro-4-difluoromethoxyphenyl)ureido]phenyl}-1H-pyrrole-3-carboxylate;

Ethyl 5-carbamoyl-4-{4-[3-(3,5-dimethylphenyl)ureido]phenyl}-1H-pyrrole-3-carboxylate;

5-Carbamoyl-4-{4-[3-(2-fluoro-5-trifluoromethylphenyl)ureido]phenyl}-1H-pyrrole-3-carboxylic acid;

4-(2,4-Dimethoxybenzylamino)carbonyl-3-{4-[3-(2-fluoro-5-trifluoromethyl-phenyl)ureido]phenyl}-1H-pyrrole-2-carboxamide;

3-{4-[3-(2-Fluoro-5-trifluoromethylphenyl)ureido]phenyl}-1H-pyrrole-2,4-dicarboxamide;

3-{4-[3-(2-Fluoro-5-trifluoromethylphenyl)ureido]phenyl}-4-(4-methylpiperazine-1-carbonyl)-1H-pyrrole-2-carboxamide;

3-{4-[3-(2-Fluoro-5-trifluoromethylphenyl)ureido]phenyl}-4-(pyrrolidine-1-carbonyl)-1H-pyrrole-2-carboxamide;

2-Dimethylaminoethyl 5-carbamoyl-4-{4-[3-(2-fluoro-5-trifluoromethylphenyl)ureido]phenyl}-1H-pyrrole-3-carboxylate;

4-Chloro-3-{4-[3-(2-fluoro-5-trifluoromethylphenyl)ureido]phenyl}-1H-pyrrole-2-carboxamide;

5-Chloro-3-{4-[3-(2-fluoro-5-trifluoromethylphenyl)ureido]phenyl}-1H-pyrrole-2-carboxamide; and 5-{4-[3-(2-Fluoro-5-trifluoromethylphenyl)ureido]phenyl}-3H-imidazole-4-carboxamide; or a pharmaceutically acceptable salt thereof.

17. A compound according to claim 1, characterized in that it is:

1) in achiral form, or
2) in racemic form, or
3) enriched in one stereoisomer, or
4) enriched in one enantiomer;

and in that it is optionally salified.

18. A pharmaceutical composition comprising a compound according to claim 1, in combination with a pharmaceutically acceptable excipient.

19. A pharmaceutical composition comprising a compound according to claim 16, in combination with a pharmaceutically acceptable excipient.

* * * * *

UNITED STATES PATENT AND TRADEMARK OFFICE
CERTIFICATE OF CORRECTION

PATENT NO. : 7,560,571 B2  Page 1 of 1
APPLICATION NO. : 11/832206
DATED : July 14, 2009
INVENTOR(S) : Baptiste Ronan et al.

It is certified that error appears in the above-identified patent and that said Letters Patent is hereby corrected as shown below:

In column 6, line 28, delete "6-mercaptomurine" and insert -- 6-mercaptopurine --, therefor.

In column 10, line 6-7, delete "perhydronapthyl" and insert -- perhydronaphthyl --, therefor.

In column 14, (under Scheme 3), line 60-66, delete " 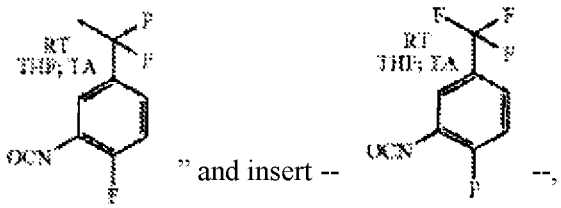 " and insert -- --, therefor.

In column 20, line 5, delete "Plafform" and insert -- Platform --, therefor.

In column 49, line 45, delete "carbamoyl4" and insert -- carbamoyl-4 --, therefor.

In column 50, line 61, before "98/1/1" insert -- ( --.

Signed and Sealed this

Twentieth Day of July, 2010

David J. Kappos
*Director of the United States Patent and Trademark Office*